US009534248B2

(12) United States Patent
Gambhir et al.

(10) Patent No.: US 9,534,248 B2
(45) Date of Patent: Jan. 3, 2017

(54) TUMOR-SPECIFIC MINICIRCLES FOR CANCER SCREENING

(71) Applicant: The Board of Trustees of the Leland Stanford Junior University, Palo Alto, CA (US)

(72) Inventors: Sanjiv S. Gambhir, Portola Valley, CA (US); John A. Ronald, Pacifica, CA (US)

( * ) Notice: Subject to any disclaimer, the term of this patent is extended or adjusted under 35 U.S.C. 154(b) by 0 days.

(21) Appl. No.: 14/480,861

(22) Filed: Sep. 9, 2014

(65) Prior Publication Data
US 2015/0071859 A1    Mar. 12, 2015

Related U.S. Application Data

(60) Provisional application No. 61/875,720, filed on Sep. 10, 2013.

(51) Int. Cl.
*A61K 48/00*    (2006.01)
*C12Q 1/66*    (2006.01)

(52) U.S. Cl.
CPC .................. *C12Q 1/66* (2013.01); *A61K 48/00* (2013.01); *G01N 2800/7028* (2013.01)

(58) Field of Classification Search
CPC ..................................................... A61K 48/00
See application file for complete search history.

(56) References Cited

U.S. PATENT DOCUMENTS

2014/0140959 A1*    5/2014    Szalay ................. A61K 49/006
424/93.2

OTHER PUBLICATIONS

Bao et al. Activation of cancer-specific gene expression by the survivin promoter. Journal of the National Cancer Institute, vol. 94, No. 7, pp. 522-528, Apr. 3, 2002.*
Johansen et al. Increased in vitro and in vivo transgene expression levels mediated through cis-acting elements. The Journal of Gene Medicine, vol. 5, pp. 1080-1089, 2003.*
Berger et al., Secreted placental alkaline phosphatase: a powerful new quantitative indicator of gene expression in eukaryotic cells (1988) Gene 66: 1-10.
Bhang et al., Tumor-specific imaging through progression elevated gene-3 promoter-driven gene expression (2011) Nat. Med. 17: 123-129.
Bonnet et al., Systemic Delivery of DNA or siRNA Mediated by Linear Polyethylenimine (L-PEI) Does Not Induce an Inflammatory Response (2008) Pharmaceut. Res. 25: 2972-2982.
Browne et al., Cancer Screening by Systemic Administration of a Gene Delivery Vector Encoding Tumor-Selective Secretable Biomarker Expression (2011) PLoS One 6:e19530.
Chaudhuri et al., Blood-based Screening and Light Based Imaging for the Early Detection and Monitoring of Ovarian Cancer Xenografts (2003) Technol. in Cancer Res. & Treat 2: 171-180.

Chen et al., Minicircle DNA Vectors Devoid of Bacterial DNA Result in Persistent and High-Level Transgene Expression in Vivo (2003) Mol. Therapy: J. Am. Soc. Gene Therapy 8: 495-500.
Chen et al., Cancer-specific activation of the survivin promoter and its potential use in gene therapy (2004) Cancer Gene Therapy 11: 740-747.
Chen et al., Silencing of episomal transgene expression by plasmid bacterial DNA elements in vivo (2004) Gene Therapy 11: 856-864.
Darquet et al., A new DNA vehicle for nonviral gene delivery: supercoiled minicircle (1997) Gene Therapy 4: 1341-1349.
Darquet et al., Minicircle: an improved DNA molecule for in vitro and in vivo gene transfer (1999) Gene Therapy 6: 209-218.
Harrington et al., Cancer Gene Therapy: Part 2. Candidate Transgenes and their Clinical Development (2002) Clinical Oncology 14: 148-169.
Iyer et al. Bioluminescence Imaging of Systemic Tumor Targeting (2006) Human Gene Therapy 17: 125-132.
Iyer et al., Noninvasive Imaging of Enhanced Prostate-Specific Gene Expression Using a Two-Step Transcriptional Amplification-Based Lentivirus Vector (2004) Mol. Therapy 10: 545-552.
Iyer et al., Non-invasive imaging of a transgenic mouse model using a prostate-specific two-step transcriptional amplification strategy (2005) Transgenic Res. 14: 47-55.
Kay et al., A robust system for production of minicircle DNA vectors (2010) Nat. Biotechnol. 28: 1287-1289.
Li et al., A survivin-mediated oncolytic adenovirus induces non-apoptotic cell death in lung cancer cells and shows antitumoral potential in vivo (2006) J. Gene Med. 8: 1232-1242.
Lu et al., Evaluation of tumor-specific promoter activities in melanoma (2005) Gene Therapy 12: 330-338.
Ray et al., Noninvasive Imaging of Therapeutic Gene Expression Using a Bidirectional Transcriptional Amplification Strategy (2008) Mol. Therapy: J. Am. Soc. Gene Therapy 16: 1848-1856.
Van Houdt et al., The human survivin promoter: a novel transcriptional targeting strategy for treatment of glioma(2006) J. Neurosurgery 104: 583-592.

(Continued)

*Primary Examiner* — Jennifer Dunston
(74) *Attorney, Agent, or Firm* — Thomas|Horstemeyer, LLP

(57) ABSTRACT

The present disclosure encompasses embodiments of nucleic acid minicircle vectors most advantageous for the detection of tumor cells. In particular, the minicircles of the disclosure incorporate a tumor-specific promoter operably linked to a nucleotide sequence desired to be selectively expressed in a tumor cell or a tissue comprising a population of tumor cells. In embodiments of the disclosure, the minicircle vectors comprise a tumor-specific promoter operably linked to a nucleotide sequence encoding a polypeptide useful as a reporter. Accordingly, when expressed by a recipient tumor cell, the reporter may be detectable, thereby providing information such as a visual image of the tumor cell and/or its location in a tissue of the subject human or non-human animal. Tumor-specific minicircle vectors driving the expression of either secreted embryonic alkaline phosphatase or firefly luciferase and their utility validated for detecting tumors after systemic administration using blood- and/or imaging-based assays are disclosed.

4 Claims, 24 Drawing Sheets

(56) References Cited

OTHER PUBLICATIONS

Warram et al., A Genetic Strategy for Combined Screening and Localized Imaging of Breast Cancer (2011) Mol. Imaging Biol. 13: 452-461.

Warram et al., Systemic delivery of a breast cancer-detecting adenovirus using targeted microbubbles (2012) Cancer Gene Therapy 19: 545-552.

Zuo et al., Minicircle-oriP-IFNy: A Novel Targeted Gene Therapeutic System for EBV Positive Human Nasopharyngeal Carcinoma (2011) PLoS One 6: e19407, printed as pp. 1/12-12/12.

* cited by examiner

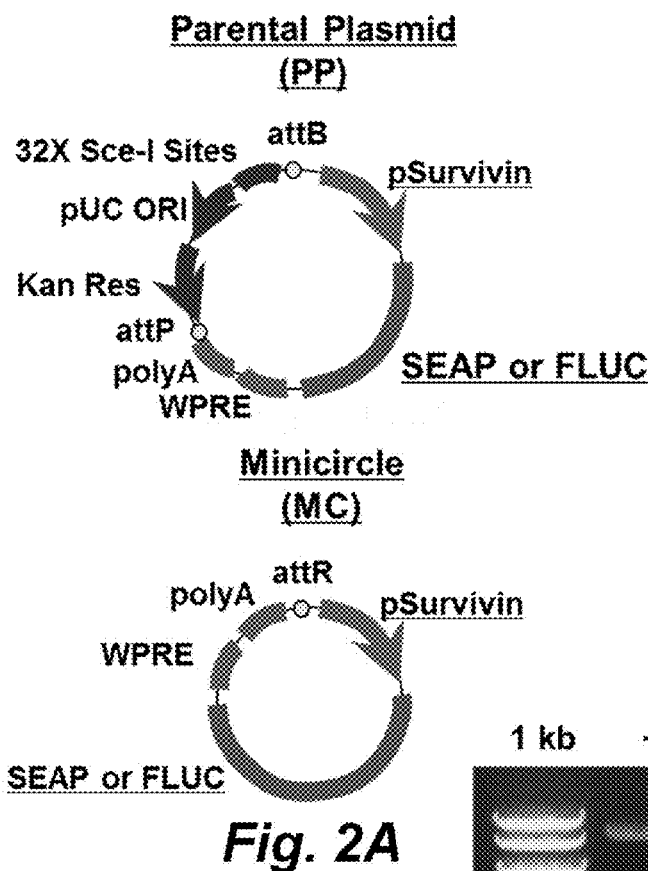
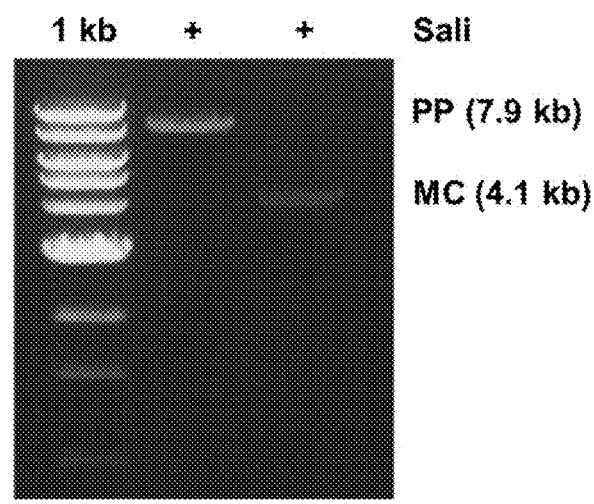
Fig. 2A
Fig. 2B

MC-pSurv-SEAP-WPRE-pA (SEQ ID NO: 1)
cccaactggggtaacctttgggctccccgggcgcgactagtaataaaatatctttattttcatta
catctgtgtgttggttttttgtgtgaatcgatagtactaacatacgctctccatcaaaacaaaacg
aaacaaaacaaactagcaaaataggctgtccccagtgcaagtgcaggtgccagaacatttctctac
tagtgccatagaaccagagaagtgagtggatgtgatgccagctccagaagtgactccagaacacc
ctgttccaaagcagaggacacactgattttttttttaataggctgcaggacttactgttggtggga
cgccctgctttgcgaagggaaggaggagtttgccctgagcacaggccccaccctccactgggct
ttccccagctccttgtcttcttatcacggtagtggcccagtccctggccctgactccagaaggt
ggcctcctggaaacccaggtcgtgcagtcaacgatgtactcgccgggacagcgatgtctgctgca
ctccatccctccctgttcatttgtccttcatgcccgtctggagtagatgctttttgcagaggtgg
caccctgtaaagctctcctgtctgactttttttttttttttagactgagttttgctcttgttgcct
aggctggagtgcaatggcacaatctcagctcactgcaccctctgcctcccgggttcaagcgattct
cctgcctcagcctcccgagtagttgggattacaggcatgcaccaccacgcccagctaattttgta
tttttagtagagacaaggtttcaccgtgatggccaggctggtcttgaactccaggactcaagtgat
gctcctgcctaggcctctcaaagtgttgggattacaggcgtgagccactgcacccggcctgcacgc
gttctttgaaagcagtcgaggggcgctaggtgtgggcagggacgagctggcgcggcgtcgctggg
tgcaccgcgaccacgggcagagccacgcggcgggaggactacaactcccggcacaccccgcgccgc
ccgcctctactcccagaaggccgcggggggtggaccgcctaagagggcgtgcgctcccgacatgc
ccgcggcgcgccattaaccgccagatttgaatcgcgggacccgttggcagaggtgggaattcacc
ggtcaccatggttctggggccctgcatgctgctgctgctgctgctgggcctgaggctacagct
ctccctgggcatcatcccagttgaggaggagaacccggacttctggaaccgcgaggcagccgaggc
cctgggtgccgccaagaagctgcagcctgcacagacagccgccaagaacctcatcatcttcctggg
cgatgggatgggggtgtctacggtgacagctgccaggatcctaaaagggcagaagaaggacaaact
ggggcctgagatacccctggctatggaccgcttcccatatgtggctctgtccaagacatacaatgt
agacaaacatgtgccagacagtggagccacagccacggcctacctgtgcggggtcaagggcaactt
ccagaccattggcttgagtgcagccgccgctttaaccagtgcaacacgacacgcggcaacgagt
catctccgtgatgaatcgggccaagaaagcagggaagtcagtgggagtggtaaccaccacacgagt
gcagcacgcctcgccagccggcacctacgcccacacggtgaaccgcaactggtactcggacgccga
cgtgcctgcctcggccgccaggagggtgccaggacatcgctacgcagctcatctccaacatgga
cattgatgtgatcctgggtggaggccgaaagtacatgtttcgcatgggaaccccagaccctgagta
cccagatgactacagccaaggtgggaccaggctggacgggaagaatctggtgcaggaatggctggc
gaagcgccagggtgcccggtatgtgtggaaccgcactgagctcatgcaggcttccctggacccgtc
tgtgacccatctcatgggtctctttgagcctggagacatgaaatacgagatccaccgagactccac
actggaccctccctgatggagatgacagaggctgccctgcgcctgctgagcaggaaccccgcgg
cttcttcctcttcgtggagggtggtcgcatcgaccacggtcatcacgaaagcagggcttaccgggc
actgactgagacgatcatgttcgacgacgccattgagagggcgggccagctcaccagcgaggagga
cacgctgagcctcgtcactgccgaccactccacgtcttctccttcggaggctaccccctgcgagg
gagctccatcttcgggctggccctggcaaggcccgggacaggaaggcctacacggtcctcctata
cggaaacggtccaggctatgtgctcaaggacggcgcccggccggatgttaccgagagcgagagcgg
gagccccgagtatcggcagcagtcagcagtgcccctggacgaagagacccacgcaggcgaggacgt
ggcggtgttcgcgcgcggcccgcaggcgcacctggttcacggcgtgcaggagcagaccttcatagc
gcacgtcatggccttcgccgcctgcctggagccctacaccgcctgcgacctggcgccccgccgg
caccaccgacgccgcgcacccggggcggtcccggtccaagcgtctggattgagctagcttcgaatt
taaatcggatccctgcaggagctcgtcgacaatcaacctctggattacaaaat

```
ttgtgaaagattgactggtattcttaactatgttgctccttttacgctatgtggatacgctgctt
taatgcctttgtatcatgctattgcttcccgtatggctttcattttctcctccttgtataaatcc
tggttgctgtctctttatgaggagttgtggcccgttgtcaggcaacgtggcgtggtgtgcactgt
gtttgctgacgcaaccccactggttggggcattgccaccacctgtcagctcctttccgggactt
tcgctttccccctccctattgccacggcggaactcatcgccgcctgccttgcccgctgctggaca
ggggctcggctgttgggcactgacaattccgtggtgttgtcggggaaatcatcgtcctttccttg
gctgctcgcctgtgttgccacctggattctgcgcgggacgtccttctgctacgtcccttcggccc
tcaatccagcggaccttccttcccgcggcctgctgccggctctgcggcctcttccgcgtcttcgc
cttcgccctcagacgagtcggatctcccctttgggccgcctcccgcctggtacctttaagaccaa
tgacttacaaggcagctgtagatcttagccacttttaaaagaaaagggggactggaagggcta
attcactcccaacgaaaataagatctgcttttttgcttgtactgggtctctctggttagaccagat
ctgagcctgggagctctctggctaactagggaaccactgcttaagcctcaataaagcttgcctt
gagtgcttcaagtagtgtgtgcccgtctgttgtgtgactctggtaactagagatccctcagaccc
ttttagtcagtgtggaaaatctctagcagtagtagttcatgtcatcttattattcagtatttata
acttgcaaagaaatgaatatcagagagtgagaggaacttgtttattgcagcttataatggttaca
aataaagcaatagcatcacaaatttcacaaataaagcatttttttcactgcattctagttgtggt
ttgtccaaactcatcaatgtatcttatcatgtctggctctagctatcccgcccctaactccgccc
agttccgcccattctccgcccctcccgcccctaactccgcccaatggctgactaatttttttat
ttatgcagaggccgaggccgcctcggcctctgagctattccagaagtagtgaggaggcttttttg
gaggcctagacttttgcagatcgacccatgggggcccg
```

Fig. 13-cont'd

```
MC-pSurv-Luc2-WPRE-pA (SEQ ID NO: 2)
ccccaactggggtaacctttgggctccccgggcgcgactagtaataaaatatctttatttcat
tacatctgtgtgttggttttttgtgtgaatcgatagtactaacatacgctctccatcaaaacaa
aacgaaacaaaacaaactagcaaaataggctgtccccagtgcaagtgcaggtgccagaacattt
ctctactagtgaattgatgccatagaaccagagaagtgagtggatgtgatgcccagctccagaa
gtgactccagaacaccctgttccaaagcagaggacacactgatttttttttaataggctgcag
gacttactgttggtgggacgccctgctttgcgaagggaaaggaggagtttgccctgagcacagg
cccccaccctccactgggctttccccagctccttgtcttcttatcacggtagtggcccagtcc
ctggcccctgactccagaaggtggcctcctggaaacccaggtcgtgcagtcaacgatgtactc
gccgggacagcgatgtctgctgcactccatccctccctgttcatttgtccttcatgcccgtct
ggagtagatgcttttgcagaggtggcaccctgtaaagctctcctgtctgacttttttttttt
tttagactgagttttgctcttgttgcctaggctggagtgcaatggcacaatctcagctcactgc
accctctgcctcccgggttcaagcgattctcctgcctcagcctcccgagtagttgggattacag
gcatgcaccaccacgcccagctaattttgtatttttagtagagacaaggttcaccgtgatgg
ccaggctggtcttgaactccaggactcaagtgatgctcctgcctaggcctctcaaagtgttggg
attacaggcgtgagccactgcacccggcctgcacgcgttctttgaaagcagtcgagggggcgct
aggtgtgggcagggacgagctggcgcggcgtcgctgggtgcaccgcgaccacgggcagagccac
gcggcgggaggactacaactcccggcacacccgcgccgccccgcctctactcccagaaggccg
cgggggtggaccgcctaagagggcgtgcgctcccgacatgccccgcggcgcgccattaaccgc
cagatttgaatcgcgggacccgttggcagaggtggaagcttggcaatccggtactgttggtaaa
gccaccatggaagatgccaaaaacattaagaagggcccagcgccattctacccactcgaagacg
ggaccgccggcgagcagctgcacaaagccatgaagcgctacgccctggtgcccggcaccatcgc
ctttaccgacgcacatatcgaggtggacattacctacgccgagtacttcgagatgagcgttcgg
ctggcagaagctatgaagcgctatgggctgaatacaaaccatcggatcgtggtgtgcagcgaga
atagcttgcagttcttcatgccgtgttgggtgccctgttcatcggtgtggctgtggccccagc
taacgacatctacaacgagcgcgagctgctgaacagcatgggcatcagccagcccaccgtcgta
ttcgtgagcaagaaagggctgcaaaagatcctcaacgtgcaaaagaagctaccgatcatacaaa
agatcatcatcatggatagcaagaccgactaccagggcttccaaagcatgtacaccttcgtgac
ttcccatttgccacccggcttcaacgagtacgacttcgtgcccgagagcttcgaccgggacaaa
accatcgccctgatcatgaacagtagtggcagtaccggattgcccaagggcgtagccctaccgc
accgcaccgcttgtgtccgattcagtcatgcccgcgacccatcttcggcaaccagatcatccc
cgacaccgctatcctcagcgtggtgccatttcaccacggcttcggcatgttcaccacgctgggc
tacttgatctgcggctttcgggtcgtgctcatgtaccgcttcgaggaggagctattcttgcgca
gcttgcaagactataagattcaatctgccctgctggtgcccacactatttagcttcttcgctaa
gagcactctcatcgacaagtacgacctaagcaacttgcacgagatcgccagcggcggggcgccg
ctcagcaaggaggtaggtgaggccgtggccaaacgcttccacctaccaggcatccgccagggct
acggcctgacagaaacaaccagcgccattctgatcacccccgaaggggacgacaagcctggcgc
agtaggcaaggtggtgcccttcttcgaggctaaggtggtggacttggacaccggtaagacactg
ggtgtgaaccagcgcggcgagctgtgcgtccgtggccccatgatcatgagcggctacgttaaca
accccgaggctacaaacgctctcatcgacaaggacggctggctgcacagcggcgacatcgccta
ctgggacgaggacgagcacttcttcatcgtggaccggctgaagagcctgatcaaatacaaggc
taccaggtagcccagccgaactggagagcatcctgctgcaacaccccaacatcttcgacgccg
gggtcgccggcctgcccgacgacgatgc
```

*Fig. 14* cggcgagctgcccgccgcagtcgtcgtgctggaacacggtaaaaccatgaccgagaaggaga
tcgtggactatgtggccagccaggttacaaccgccaagaagctgcgcggtggtgttgtgttc
gtggacgaggtgcctaaaggactgaccggcaagttggacgcccgcaagatccgcgagattct
cattaaggccaagaagggcggcaagatcgccgtgtaatctagagctagcgaattcagatctg
atatctctagagtcgagctagcttcgaatttaaatcggatccctgcaggagctcgtcgacaa
tcaacctctggattacaaaatttgtgaaagattgactggtattcttaactatgttgctcctt
ttacgctatgtggatacgctgctttaatgcctttgtatcatgctattgcttcccgtatggct
ttcattttctcctccttgtataaatcctggttgctgtctctttatgaggagttgtggcccgt
tgtcaggcaacgtggcgtggtgtgcactgtgtttgctgacgcaacccccactggttgggca
ttgccaccacctgtcagctcctttccgggactttcgctttcccctccctattgccacggcg
gaactcatcgccgcctgccttgcccgctgctggacagggctcggctgttgggcactgacaa
ttccgtggtgttgtcggggaaatcatcgtcctttccttggctgctcgcctgtgttgccacct
ggattctgcgcgggacgtccttctgctacgtccttcggccctcaatccagcggaccttcct
tcccgcggcctgctgccggctctgcggcctcttccgcgtcttcgccttcgccctcagacgag
tcggatctcctttgggccgcctccccgcctggtacctttaagaccaatgacttacaaggca
gctgtagatcttagccacttttttaaaagaaaagggggggactggaagggctaattcactccca
acgaaaataagatctgctttttgcttgtactgggtctctctggttagaccagatctgagcct
gggagctctctggctaactagggaacccactgcttaagcctcaataaagcttgccttgagtg
cttcaagtagtgtgtgcccgtctgttgtgtgactctggtaactagagatccctcagaccctt
ttagtcagtgtggaaaatctctagcagtagtagttcatgtcatcttattattcagtatttat
aacttgcaaagaaatgaatatcagagagtgagaggaacttgtttattgcagcttataatggt
tacaaataaagcaatagcatcacaaatttcacaaataaagcatttttttcactgcattctag
ttgtggtttgtccaaactcatcaatgtatcttatcatgtctggctctagctatccgcccct
aactccgcccagttccgcccattctccgcccctccgcccctaactccgcccaatggctgac
taatttttttatttatgcagaggccgaggccgcctcggcctctgagctattccagaagtag
tgaggaggcttttttggaggcctagacttttgcagatcgaccatggggggcccg

*Fig. 14-cont'd*

In Vivo BLI

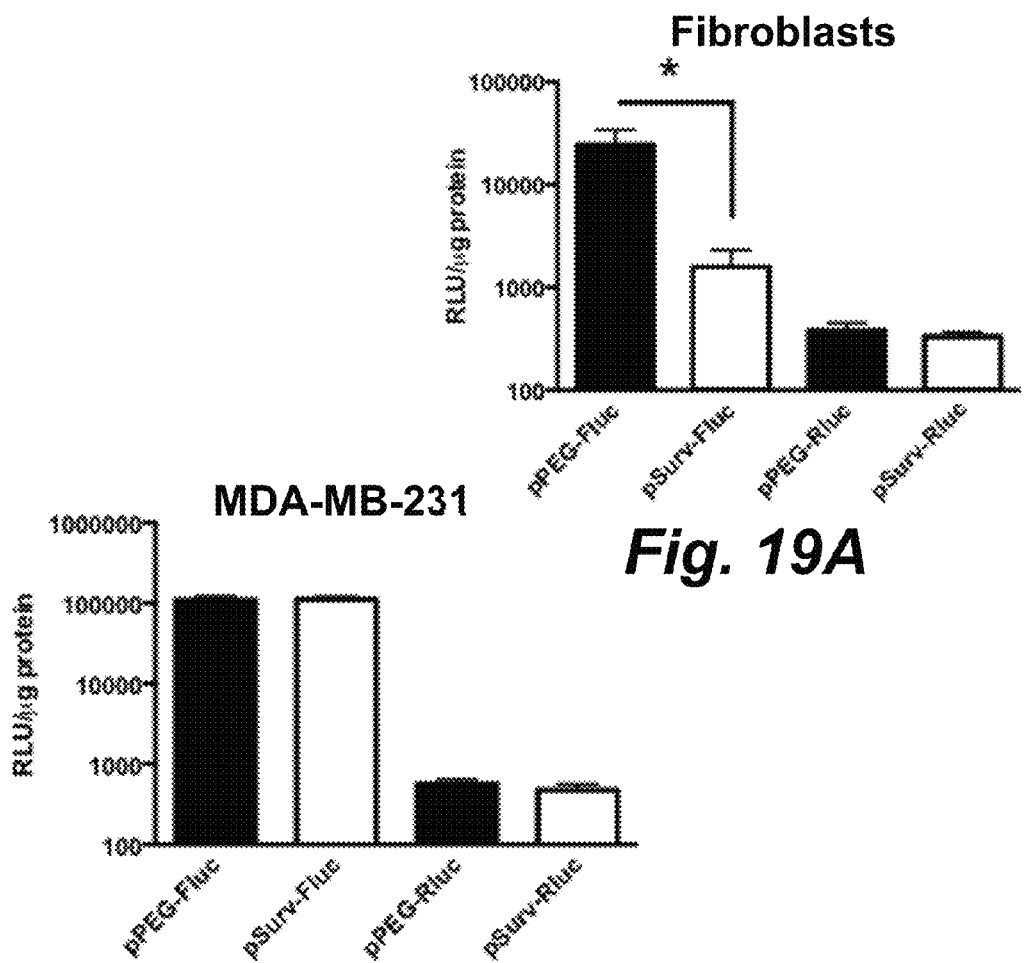
Fig. 19A
Fig. 19B
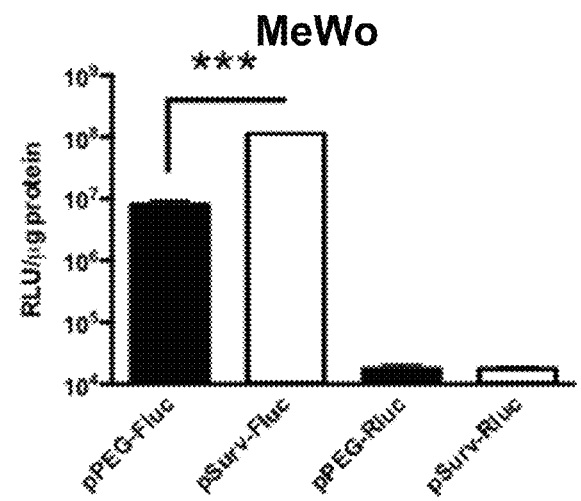
Fig. 19C

| mg SEAP in 25 ml plasma | % CV |
|---|---|
| 3e-02 | 2.16 |
| 3e-03 | 3.10 |
| 3e-04 | 1.47 |
| 3e-05 | 0.91 |
| 3e-06 | 1.09 |
| 3e-07 | 3.82 |

TUMOR-SPECIFIC MINICIRCLES FOR CANCER SCREENING

CROSS-REFERENCE TO RELATED APPLICATIONS

This application claims priority to U.S. Provisional Patent Application Ser. No. 61/875,720 entitled "Tumor-Specific Minicircles for Cancer Screening via Blood-Based and Molecular Imaging Assays" and filed Sep. 10, 2013, the entirety of which is hereby incorporated by reference.

STATEMENT REGARDING FEDERALLY SPONSORED RESEARCH OR DEVELOPMENT

This invention was made with Government support under contracts NCI ICMIC P50CA114747, NCI RO1 CA082214, and NCI RO1 CA135486 awarded by the National Institutes of Health. The government has certain rights in the invention.

SEQUENCE LISTING

The present disclosure includes a sequence listing incorporated herein by reference in its entirety.

FIELD OF THE DISCLOSURE

The present disclosure relates to recombinant nucleic acid minicircles useful for the tumor-specific expression of heterologous coding nucleic acid sequences by a cell or subject human or non-human animal. The present disclosure further relates to methods of specifically detecting a tumor cell or population of tumor cells. The present disclosure even further relates to methods of detectably imaging a tumor cell or population of tumor cells.

BACKGROUND

Cancer is an enormous global health problem. The American Cancer Society estimates that in 2008 alone there were an estimated 12.7 million new diagnoses of cancer and 7.6 million deaths due to cancer. The time at which cancer is detected, both prior to initial cancer diagnosis and during tumor recurrence, is one of the most important factors affecting patient outcome since if detected early, current treatments are likely to be more effective. Unfortunately, the majority of cancers are detected relatively late, leading to high mortality rates. These rates are expected to double by 2030 unless more effective detection strategies and treatments are developed. To stem the tremendous loss of life due to this terrible disease, a broadly applicable tool capable of detecting cancer in its earliest stages is urgently needed.

Two current paradigms for improving cancer detection include the development of blood-based assays that detect endogenous cancer biomarkers (e.g. protein, microRNA, circulating tumor DNA, circulating tumor cells, etc.) that are shed or released into the bloodstream, and molecular imaging assays that utilize biomarker-targeted imaging probes to better visualize tumors that are undetectable with conventional anatomical imaging.

Blood assays are highly attractive as they facilitate affordable cancer screening programs but often suffer from sensitivity and specificity issues due to low blood biomarker concentrations (Nagrath et al., (2007) *Nature* 450: 1235-1239), rapid in vivo and ex vivo biomarker degradation (Haun et al., (2011) *Sci. Translational Med.* 3: 71ra16), and highly variable background expression in non-malignant tissues (Diamandis E P (2010) *J. National Cancer Inst.* 102: 1462-1467). Using current clinical biomarker assays, it has been estimated that a tumor can grow for 10-12 years and reach a spherical diameter greater than 2.5 cm before endogenous blood biomarker amounts reach sufficient levels to indicate disease (Hori & Gambhir (2011) *Sci. Translational Med.* 3: 109ra116). Of the thousands of potential blood biomarkers reported, less than 1% are used in the clinic (7), and the implementation of new blood biomarkers into the clinical setting is decreasing due to their lack of validated specificity and diagnostic value (Haun et al., (2011) *Sci. Translational Med.* 3: 71ra16; Kern S E (2012) *Cancer Res.* 72: 6097-6101). Overall, while enormous effort has been devoted to developing tools for detecting endogenous cancer blood biomarkers, there have been very few successes. Thus new strategies and tools capable of sensitive and specific cancer detection are urgently needed.

SUMMARY

One aspect of the disclosure encompasses embodiments of a recombinant nucleic acid minicircle vector comprising a nucleotide sequence operably linked to a tumor-specific gene expression promoter and expressible at a level greater by a recipient tumor cell than by a non-tumor cell.

In the embodiments of this aspect of the disclosure the tumor-specific gene expression promoter may be selected from the group consisting of: a survivin promoter, a CXCR4 promoter, a Hexokinase type II promoter, a TRPM4 (Transient Receptor Potential-Melastatin 4) promoter, a stromelysin 3 promoter, a surfactant protein A promoter, a secretory leukoprotease inhibitor (SLPI) promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein (DF3, MUC1) promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter; a villin promoter, and an albumin promoter.

In some embodiments of this aspect of the disclosure, the nucleotide sequence operably linked to the tumor-specific promoter can be expressed as a polypeptide.

In some embodiments of this aspect of the disclosure, the nucleotide sequence operably linked to the tumor-specific promoter can encode a reporter polypeptide.

In some embodiments of this aspect of the disclosure, the reporter polypeptide may be an MRI reporter, a PET reporter; a SPECT reporter, a photoacoustic reporter, a bioluminescent reporter, or any combination thereof.

In some embodiments of this aspect of the disclosure, the polypeptide can be secreted embryonic alkaline phosphatase (SEAP).

In some embodiments of this aspect of the disclosure, the polypeptide can be a bioluminescent reporter.

Another aspect of the disclosure encompasses embodiments of a pharmaceutically acceptable composition comprising a recombinant nucleic acid minicircle vector comprising a nucleotide sequence operably linked to a tumor-specific gene expression promoter and expressible at a level greater by a recipient tumor cell than by a non-tumor cell, and a pharmaceutically acceptable carrier, wherein: (i) the tumor-specific gene expression promoter can be selected from the group consisting of: a survivin promoter, a CXCR4 promoter, a Hexokinase type II promoter, a TRPM4 (Transient Receptor Potential-Melastatin 4) promoter, a stromelysin 3 promoter, a surfactant protein A promoter, a secretory leukoprotease inhibitor (SLPI) promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein (DF3, MUC1) promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter; a villin promoter, and an albumin promoter; and (ii) the nucleotide sequence operably linked to the tumor-specific promoter can be expressed as a polypeptide encoding an MRI reporter, a PET reporter; a SPECT reporter, a photoacoustic reporter, a bioluminescent reporter, or any combination thereof.

In some embodiments of this aspect of the disclosure, the recombinant nucleic acid minicircle vector can have the nucleic acid sequence according to SEQ ID NO: 1 or SEQ ID NO: 2.

Yet another aspect of the disclosure encompasses embodiments of a method of detecting a tumor cell in a human or non-human subject, comprising the steps of: (i) delivering to a first subject human or non-human animal a pharmaceutically acceptable composition comprising a recombinant nucleic acid minicircle vector comprising a nucleotide sequence operably linked to a tumor-specific gene expression promoter and expressible at a level greater by a recipient tumor cell than by a non-tumor cell, and a pharmaceutically acceptable carrier, wherein: (a) the tumor-specific gene expression promoter can be selected from the group consisting of: a survivin promoter, a CXCR4 promoter, a Hexokinase type II promoter, a TRPM4 (Transient Receptor Potential-Melastatin 4) promoter, a stromelysin 3 promoter, a surfactant protein A promoter, a secretory leukoprotease inhibitor (SLPI) promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein (DF3, MUC1) promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter; a villin promoter, and an albumin promoter; and (b) the nucleotide sequence operably linked to the tumor-specific promoter can be expressed as a polypeptide encoding an MRI reporter, a PET reporter; a SPECT reporter, a photoacoustic reporter, a bioluminescent reporter, or any combination thereof; and (ii) detecting an expression product in the first subject, wherein said expression product is generated from the nucleotide sequence operably linked to the tumor-specific gene expression promoter of the minicircle vector, and wherein the detection of said expression product indicates the presence of a tumor cell in the first subject.

In some embodiments of this aspect of the disclosure, the expression product can be a serum polypeptide and step (ii) can comprise obtaining a serum sample from the first subject and determining the serum level of the expression product generated from the minicircle vector.

In some embodiments of this aspect of the disclosure, the expression product can be a bioluminescent polypeptide and the step (ii) can comprise generating a detectable signal derived from the expression product, measuring the level of the detectable signal generated from the minicircle vector, and comparing the level of the signal from the first subject to that obtained from a second subject not receiving the minicircle vector, wherein an elevated level signal from the first subject compared to that level obtained from a second subject indicates that the first subject comprises a tumor cell or population of tumor cells.

In some embodiments of this aspect of the disclosure, the step (ii) can further comprise non-invasively detecting the detectable signal, converting said signal into an image, overlaying said image with an image of the first subject, and locating the detectable signal relative to the first subject, thereby determining the position of a tumor cell or population of tumor cells in the first subject.

Strategies for improved cancer diagnosis have traditionally relied on measurement of endogenous molecules that are over-expressed in cancer cells either via molecular imaging or blood-based assays. A challenge of these strategies is often significant expression within non-cancerous tissues, leading to high background levels and confounding results. An alternative strategy is to utilize promoters of tumor-specific (TS) proteins in exogenously-delivered gene vectors in order to drive the expression of unique reporter genes (RGs) strictly within tumors. For this strategy to become a reality, safety, specificity, and sensitivity are of utmost importance. While safer than viral vectors, two drawbacks of non-viral vectors have been low gene transfer rates and transient expression profiles. Minicircles (MCs) are plasmids that lack a bacterial backbone and are advantageous to overcome the above key issues.

BRIEF DESCRIPTION OF THE DRAWINGS

Many aspects of the disclosure can be better understood with reference to the following drawings.

FIGS. 2A-2B illustrate the design and construction of tumor-activatable vectors.

FIG. 2A illustrates vector maps of both Survivin promoter (pSurv)-driven parental plasmids (PP; top) and MCs (bottom). These constructs encoded the reporter protein secreted embryonic alkaline phosphatase (SEAP). The PP and MC have the identical transcription unit (pSurv-SEAP-WPRE-polyA) but the MC lacks the prokaryotic backbone (light grey). WPRE (Woodchuck Hepatitis virus posttranscriptional regulatory element (WPRE).

FIG. 2B illustrates agarose gel electrophoresis confirming the ability to generate both PP (7.9 kb) and MC (4.1 kb).

FIG. 13 illustrates the nucleic acid sequence of minicircle MC-pSurv-SEAP-WPRE-pA.

FIG. 14 illustrates the nucleic acid sequence of minicircle MC-pSurv-Luc2-WPRE-pA.

FIGS. 16A-16C illustrate human melanoma tumor development following intravenous cell administration in nude mice (n=7) monitored using bioluminescence imaging (BLI) (left images). Representative BLI images showed tumor growth primarily within the lung and individual mice had a wide range of tumor burden within 3 days prior to MC administration. The BLI scales in FIGS. 16A and 16B are the same, but that of FIG. 16C is one order of magnitude lower. Tumor-activatable MCs were administered systemically and SEAP levels were measured before (Day 0) and up to 14 days following administration (right graphs). Varying SEAP concentrations were detected in tumor-bearing mice over the 14-day period.

FIG. 16D illustrates healthy (tumor-free) mice that received either MC (Control+MC; n=7) or 5% glucose carrier only (Control-MC; n=5). No statistically significant differences in plasma SEAP levels were detected between these two groups. Importantly, across all mice regardless of tumor burden, significantly higher plasma SEAP concentration was detected in tumor-bearing mice receiving MC between days 3 to 14 compared to both control groups (#*p<0.05; ##**p<0.01). Data is expressed as mean±SEM.

FIG. 17A: Area under the curve (AUC) analysis of plasma SEAP measurements over 2 weeks revealed significant differences between tumor-bearing mice receiving MCs (n=7) compared to both healthy mice receiving MCs (n=7) or 5% glucose (n=5) (*p<0.05; **p<0.01). Data is expressed as mean±SD.

FIG. 17B: ROC analysis revealed a significant ability of the tumor-activatable MC system to differentiate tumor-bearing from healthy subjects by measuring and computing plasma SEAP AUC.

FIG. 17C: Correlational analysis of SEAP AUC measurements and lung tumor burden (as measured by BLI lung average radiance). Across 6 mice a significant positive correlation was noted between these two measures, showing the ability of our tool to assess tumor burden provided that the tumor is in one location. One mouse was removed from analysis (square symbol) since this mouse had tumors in both the lungs and multiple metastatic foci outside the lungs (BLI measurement was taken from just within lung explaining overall low BLI signal in this mouse). This mouse had a higher SEAP AUC level than would be expected based on its lung tumor burden.

FIG. 18A illustrates representative BLI images 48 hours post-injection. Image scale for the pCMV mouse is 2 orders of magnitude higher than all other mice. BLI signal, primarily in the lungs, was seen in all mice receiving Luc2 plasmid.

FIG. 18B illustrates region-of-interest analysis over the entire mouse performed on BLI images, revealing significantly higher (*p<0.05; about 100-fold) BLI signal in mice receiving pCMV-Luc2 plasmids compared to all other mice (*p<0.05). A significantly higher (*p<0.05) BLI signal was also observed in pPEG mice compared to mock-injected mice. Although qualitatively higher BLI signal was notable in pSurv mice compared to mock-injected mice, quantitative measures only revealed a trend (p=0.16) towards higher BLI signal. Thus in this mouse strain, Luc2 expression in normal tissues was lowest with the tumor-specific pSurv.

FIG. 18C illustrates that 48 h after plasmid injection, ex vivo analysis of Luc2 activity across numerous tissues revealed significantly higher (*p<0.05) expression with pCMV compared to all other groups. With pPEG, significantly higher (*p<0.05) Luc2 activity was found in the heart, lung and spleen compared to mock-injected animals. With pSurv, significantly higher (*p<0.05) Luc2 activity was in the spleen and a trend (p=0.13) towards higher activity in the lung.

FIG. 18D illustrates that the only tissue showing higher hRluc activity above background was the lung (values presented are normalized to average background values from mock-injected mice). Due to this, Luc2 values determined from both imaging (FIG. 18B) and ex vivo tissue analysis (FIG. 18C) are not normalized by hRluc values. No significant differences in hRluc values within the lungs were seen across the 3 promoter mouse groups. Thus, differences Luc2 measurements across the 3 groups are unlikely to be related to differences in transfection efficiency but to differences in promoter activity. Data is expressed as mean±SD.

FIGS. 19A-19C illustrate a comparison of tumor-specific promoter activities in primary human fibroblasts and human cancer cell lines. Primary human fibroblasts, MDA-MB-231 cells (human breast cancer) and MeWo cells (human melanoma) were transfected with pPEG- or pSurv-driven plasmids (1 μg) expressing Luc2 and co-transfected with a promoterless plasmid expressing hRluc (50 ng) to normalize for transfection efficiency. No differences in Rluc transfection efficiency were noted in any of the 3 cell types. pPEG-driven plasmids led to significantly higher Luc2 activity in fibroblasts than pSurv ($*p<0.05$). pSurv-driven plasmids led to significantly higher Luc2 activity in MeWo cells ($***p<0.001$) and equivalent activity in MDA-MB-231 cells. Data is expressed as mean±SD.

FIG. 21A illustrates mice that received systemic administration of either MCs (n=4) or PPs (n=5) expressing hRluc driven by the strong constitutive EF1 promoter after complexation with PEI (40 μg; N/P=8). BLI imaging was performed on days 1, 2, 3, 5 and 7 using the substrate coelenterazine. Representative images show higher BLI signal in MC-administered mice at all time points examined. Signal from a mouse receiving a 5% glucose injection is shown for comparison (signal in liver is from oxidized coelenterazine).

FIG. 21B illustrates a region-of-interest analysis over the lung region showing a significantly higher BLI signal in MC versus PP mice on days 1, 2, and 5 ($*p<0.05$; $**p<0.01$). Data is expressed as mean±SD.

Figure 1:
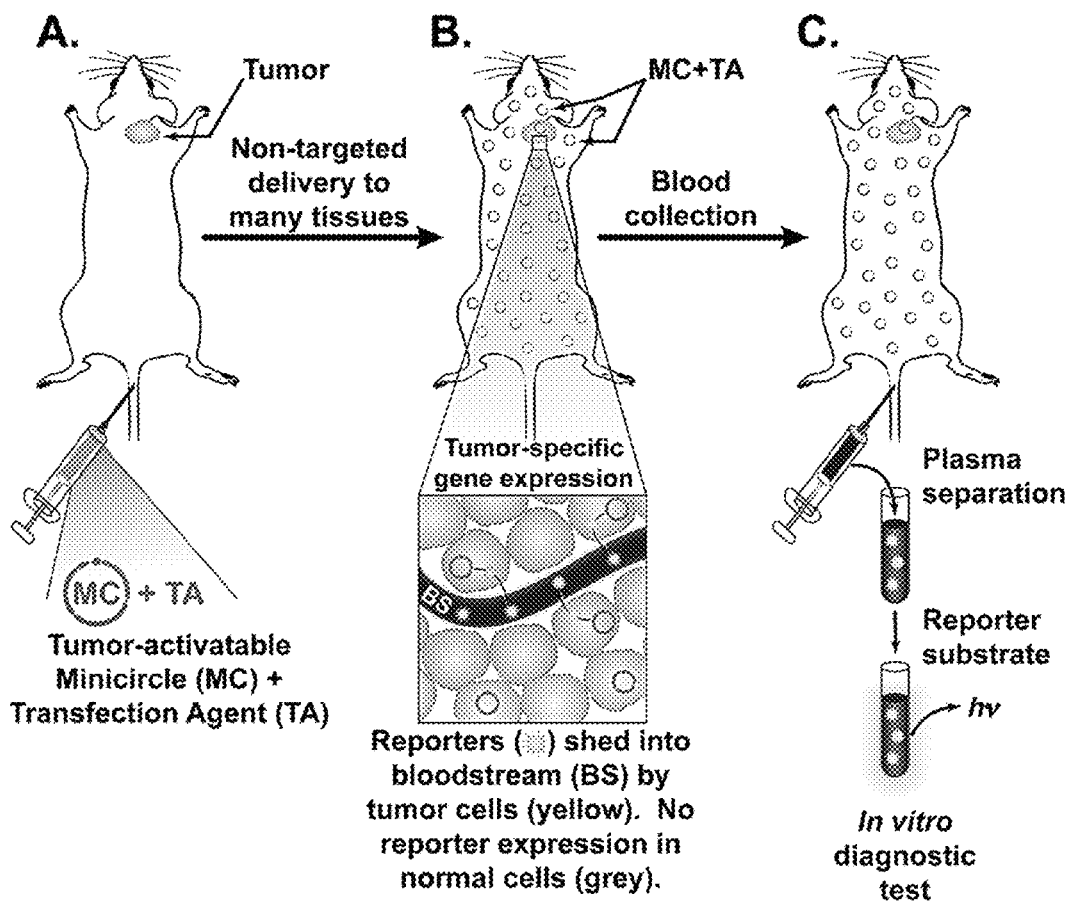
FIG. 1 schematically illustrates a blood-based tumor-activatable minicircle (MC) approach for cancer detection. (A) Tumor-activatable MCs driven by a tumor-specific promoter and encoding a secretable reporter protein are complexed with a non-targeted transfection agent (TA). These nanocomplexes are delivered systemically (via tail-vein). (B) MCs transfect many tissues but reporter protein production occurs near-exclusively within tumor cells and the expressed reporter is secreted into the bloodstream (BS). Minimal protein expression should occur in tumor-free subjects due to promoter leakiness. (C) Collection of blood and detection of the secreted reporter in plasma enables differentiation between tumor-bearing (reporter-positive) and tumor-free (reporter-negative) subjects.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, toxicology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

DEFINITIONS

The term "gene," as used herein refers to all regulatory and coding sequences contiguously associated with a single hereditary unit with a genetic function. Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes encoding proteins are comprised of "exons" (coding sequences), which may be interrupted by "introns" (non-coding sequences). In some instances complexes of a plurality of protein or nucleic acids or other molecules, or of any two of the above, may be required for a gene's function. On the other hand a gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, in an artificial chromosome, in a plasmid, in any other sort of vector, or as a separate isolated entity.

The terms "episomally replicating vector" or "episomal vector" as used herein refer to a vector which is typically not integrated into the genome of the host cell, but exists in parallel. An episomally replicating vector may be replicated during the cell cycle and in the course of this replication the vector copies are distributed statistically in the resulting cells depending on the number of the copies present before and after cell division. Replication may take place in the nucleus of the host cell, and preferably replicates during S-phase of the cell cycle. Moreover, the episomally replicating vector can be replicated at least once, i.e. one or multiple times, in the nucleus of the host cell during S-phase of the cell cycle.

The term "origin of replication" as used herein refers to a DNA sequence that is recognized by a replication initiation factor or a DNA replicase leading to replication of a plasmid containing the origin of replication. The expression "recognized by a replication initiation factor" is intended to mean that a replication initiation factor can physically interact with all or a portion of an origin of replication sequence, thereby causing or stimulating molecular mechanisms that ultimately cause all or a portion of the DNA molecule comprising the origin of replication to be replicated. The origin of replication, thus, typically comprises functionally required elements. One example for such functionally required elements are the family of repeats (FR) element or the dyad symmetry (DS) element of the EBV origin of replication (OriP). Further origin of replications comprising functionally required elements are well known in the art and are described for example in Bode et al., (2001) *Gene Ther. Mol. Biol.* 6: 33-46. The parental nucleic acid plasmid vectors of the disclosure preferably comprise at least one origin of replication.

A "vector" is capable of transferring nucleic acid sequences to target cells. For example, a vector may comprise a coding sequence capable of being expressed in a target cell. Accordingly, as used herein, the terms "vector construct," "expression vector," and "gene transfer vector," may refer to any nucleic acid construct capable of directing the expression of a gene of interest and which is useful in transferring the gene of interest into target cells.

The terms "minicircle" and "vector" as used herein refer to a small, double stranded circular DNA molecule that provides for persistent, high level expression of a sequence of interest that is present on the vector, which sequence of interest may encode a polypeptide, an shRNA, an anti-sense RNA, an siRNA, and the like. The sequence of interest is operably linked to regulatory sequences present on the minicircle vector, said regulatory sequences controlling its expression. Such minicircle vectors are described, for example in published U.S. Patent Application US20040214329, herein specifically incorporated by reference.

The overall length of a minicircle vector is sufficient to include the desired elements as described below, but not so long as to prevent or substantially inhibit to an unacceptable level the ability of the vector to enter a target cell upon contact with the cell, e.g., via system administration to the host comprising the cell. As such, the minicircle vector can be generally at least about 0.3 kb long, often at least about 1.0 kb long, whereas the parental vector may be as long as 10 kb or longer.

Minicircle vectors differ from bacterial plasmid vectors in that they lack an origin of replication, and lack drug selection markers commonly found in bacterial plasmids, e.g. β-lactamase, tetracycline-resistance ($tet^r$), kanamycin-resistance ($kan^r$) and the like. Consequently, a minicircle becomes smaller in size, allowing more efficient delivery. Minicircles lack the transgene expression silencing effect which is associated with the vector backbone nucleic acid sequences of parental plasmids from which the minicircle vectors are excised. The minicircle may be substantially free of vector sequences other than the recombinase hybrid product sequence, and the sequence of interest, i.e. a transcribed sequence and regulatory sequences required for expression.

Methods of transfecting cells are well known in the art. By "transfected" it is meant an alteration in a cell resulting from the uptake of foreign nucleic acid, usually DNA. Use of the term "transfection" is not intended to limit introduction of the foreign nucleic acid to any particular method. Thus, suitable methods include viral infection/transduction, conjugation, nanoparticle delivery, electroporation, particle gun technology, calcium phosphate precipitation, direct microinjection, and the like. The choice of method is dependent on the type of cell being transfected and the circumstances under which the transfection is taking place (i.e. in vitro, ex vivo, or in vivo). A general discussion of these methods can be found in Ausubel, et al., *Short Protocols in Molecular Biology*, 3rd ed., Wiley & Sons, 1995.

The terms "nucleic acid molecule" and "polynucleotide" as used herein refer polymeric forms of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, shRNA, single-stranded short or long RNAs, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "promoter" is a DNA sequence that directs the transcription of a polynucleotide. Typically a promoter can be located in the 5' region of a polynucleotide to be transcribed, proximal to the transcriptional start site of such polynucleotide. More typically, promoters are defined as the region upstream of the first exon; more typically, as a region upstream of the first of multiple transcription start sites. Frequently promoters are capable of directing transcription of genes located on each of the complementary DNA strands that are 3' to the promoter. Stated differently, many promoters exhibit bidirectionality and can direct transcription of a downstream gene when present in either orientation (i.e. 5' to 3' or 3' to 5' relative to the coding region of the gene). Additionally, the promoter may also include at least one control element such as an upstream element. Such elements include upstream activator regions (UARs) and optionally, other DNA sequences that affect transcription of a polynucleotide such as a synthetic upstream element.

The terms "coding sequence" and "encodes" a selected polypeptide as used herein refer to a nucleic acid molecule that is transcribed (in the case of DNA) and translated (in the case of mRNA) into a polypeptide, for example, when the nucleic acid is present in a living cell (in vivo) and placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral, eukaryotic, or prokaryotic DNA, and synthetic DNA sequences. A transcription termination sequence may be located 3' to the coding sequence, and a promoter may be located 5' to the coding sequence; along with additional control sequences if desired, such as enhancers, introns, poly adenylation site, etc. A DNA sequence encoding a polypeptide may be optimized for expression in a selected cell by using the codons preferred by the selected cell to represent the DNA copy of the desired polypeptide coding sequence.

The term "operably linked" as used herein refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The term "expression cassette" as used herein refers to any nucleic acid construct capable of directing the expression of any RNA transcript including gene/coding sequence of interest as well as non-translated RNAs, such as shRNAs, microRNAs, siRNAs, anti-sense RNAs, and the like. Such cassettes can be constructed into a "vector," "vector construct," "expression vector," or "gene transfer vector," in order to transfer the expression cassette into target cells. Thus, the term includes cloning and expression vehicles, as well as viral vectors.

The term "target cell" as used herein refers to a cell that in which a genetic modification is desired. Target cells can be isolated (e.g., in culture) or in a multicellular organism (e.g., in a blastocyst, in a fetus, in a postnatal animal, and the like).

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "detectable" refers to the ability to detect a signal over the background signal. The detectable signal is defined as an amount sufficient to yield an acceptable image using equipment that is available for pre-clinical use. A detectable signal maybe generated by one or more administrations of the probes of the present disclosure. The amount administered can vary according to factors such as the degree of susceptibility of the individual, the age, sex, and weight of the individual, idiosyncratic responses of the individual, the dosimetry, and the like. The amount administered can also vary according to instrument and digital processing related factors.

The term "in vivo imaging" as used herein refers to methods or processes in which the structural, functional, or physiological state of a living being is examinable without the need for a life-ending sacrifice.

The term "non-invasive in vivo imaging" as used herein refers to methods or processes in which the structural, functional, or physiological state of a being is examinable by remote physical probing without the need for breaching the physical integrity of the outer (skin) or inner (accessible orifices) surfaces of the body.

The "imaging moiety" may be detected either externally to a subject human or non-human animal body or via use of detectors designed for use in vivo, such as intravascular radiation or optical detectors such as endoscopes, or radiation detectors designed for intra-operative use. The imaging moiety is preferably, but is not limited to a reporter suitable for in vivo optical imaging.

The term "bioluminescence" as used herein refers to a type of chemiluminescent emission of light by biological molecules, particularly proteins. The essential condition for bioluminescence is molecular oxygen, either bound or free in the presence of an oxygenase, a luciferase, which acts on a substrate, a luciferin in the presence of molecular oxygen and transforms the substrate to an excited state, which upon return to a lower energy level releases the energy in the form of light.

The term "luciferase" as used herein refers to oxygenases that catalyze a light emitting reaction. For instance, bacterial luciferases catalyze the oxidation of flavin mononucleotide and aliphatic aldehydes, which reaction produces light. Another class of luciferases, found among marine arthropods, catalyzes the oxidation of cypridina luciferin, and another class of luciferases catalyzes the oxidation of coleoptera luciferin. Thus, "luciferase" refers to an enzyme or photoprotein that catalyzes a bioluminescent reaction. The luciferases such as firefly and *Renilla* luciferases are enzymes that act catalytically and are unchanged during the bioluminescence generating reaction. The luciferase photoproteins, such as the aequorin and obelin photoproteins to which luciferin is non-covalently bound, are changed by release of the luciferin, during bioluminescence generating reaction. The luciferase is a protein that occurs naturally in an organism or a variant or mutant thereof, such as a variant produced by mutagenesis that has one or more properties, such as thermal or pH stability, that differ from the naturally-occurring protein. Luciferases and modified mutant or variant forms thereof are well known. Reference, for example, to "*Renilla* luciferase" means an enzyme isolated from member of the genus *Renilla* or an equivalent molecule obtained from any other source, such as from another Anthozoa, or that has been prepared synthetically.

"Bioluminescent protein" refers to a protein capable of acting on a bioluminescent initiator molecule substrate to generate or emit bioluminescence.

"Bioluminescent initiator molecule" is a molecule that can react with a bioluminescent donor protein to generate bioluminescence. The bioluminescence initiator molecule includes, but is not limited to, coelenterazine, analogs thereof, and functional derivatives thereof. Derivatives of coelenterazine include, but are not limited to, coelenterazine 400a, coelenterazine cp, coelenterazine f, coelenterazine fcp, coelenterazine h, coelenterazine hcp; coelenterazine ip, coelenterazine n, coelenterazine O, coelenterazine c, coelenterazine c, coelenterazine i, coelenterazine icp, coelenterazine 2-methyl, benzyl-coelenterazine bisdeoxycoelenterazine, and deep blue coelenterazine (DBC) (described in more detail in U.S. Pat. Nos. 6,020,192; 5,968,750 and 5,874,304).

In general, coelenterazines are known to luminesce when acted upon by a wide variety of bioluminescent proteins, specifically luciferases. Useful, but non-limiting, coelenterazines are disclosed in U.S. patent application Ser. No. 10/053,482, filed Nov. 2, 2001, the disclosure of which is hereby incorporated by reference in its entirety. Coelenterazines are available from Promega Corporation, Madison, Wis. and from Molecular Probes, Inc., Eugene, Oreg. Coelenterazines may also be synthesized as described for example in Shimomura et al., (1989) *Biochem. J.* 261: 913-920; Inouye et al., (1997) *Biochem. Biophys. Res. Comm.* 233: 349-353, 1997; and Teranishi et al., (1997) *Anal. Biochem.* 249: 37-43.

The term "Survivin" as used herein refers to a protein also called baculoviral inhibitor of apoptosis repeat-containing 5 or BIRC5, is a protein that, in humans, is encoded by the BIRC5 gene. (NCBI Reference Sequence: NG_029069.1). Survivin is a member of the inhibitor of apoptosis (IAP) family. The survivin protein inhibits caspase activation, thereby leading to negative regulation of apoptosis or programmed cell death. This has been shown by disruption of survivin induction pathways leading to an increase in apoptosis and decrease in tumour growth. The survivin protein is expressed highly in most human tumours and fetal tissue, but is completely absent in terminally differentiated cells. Survivin expression is also highly regulated by the cell cycle and is only expressed in the G2-M phase. It is known that survivin localizes to the mitotic spindle by interaction with tubulin during mitosis and may play a contributing role in regulating mitosis. Regulation of survivin seems to be linked to the p53 protein. It also is a direct target gene of the Wnt pathway and is upregulated by β-catenin.

It is contemplated, however, that the minicircles of the disclosure may utilize any tumor-specific promoter operably linked to a reporter or other heterologous nucleic acid sequence desired to be expressed in a target cell. For example, but not intended to be limiting, suitable promoters known in the art include: CXCR4 promoter tumor-specific in melanomas; Hexokinase type II promoter tumor-specific in lung cancer; TRPM4 (Transient Receptor Potential-Melastatin 4) promoter is preferentially active in prostate cancer; stromelysin 3 promoter is specific for breast cancer cells (Basset et al., (1990) *Nature* 348: 699); surfactant protein A promoter specific for non-small cell lung cancer cells (Smith et al., 1994) *Hum. Gene Ther.* 5: 29-35); secretory leukoprotease inhibitor (SLPI) promoter specific for SLPI-expressing carcinomas (Garver et al., (1994) *Gene Ther.* 1: 46-50); tyrosinase promoter specific for melanoma cells (Vile et al., (1994) *Gene Ther.* 1: 307); stress-inducible grp78/BiP promoter specific for fibrosarcoma/tumorigenic cells (Gazit et al., (1995) *Cancer Res.* 55: 1660); interleukin-10 promoter specific for glioblastoma multiform cells (Nitta et al., (1994) *Brain Res.* 649: 122); α-B-crystallin/heat shock protein 27 promoter specific for brain tumor cells (Aoyama et al., (1993) *Int. J. Cancer* 55: 760); epidermal growth factor receptor promoter specific for squamous cell carcinoma, glioma, and breast tumor cells (Ishii et al., (1993) *Proc. Natl. Acad. Sci. U.S.A.* 90: 282); mucin-like glycoprotein (DF3, MUC1) promoter specific for breast carcinoma cells (Abe et al., (1993) *Proc. Natl. Acad. Sci. U.S.A.* 90: 282); mts1 promoter specific for metastatic tumors (Tulchinsky et al., (1992) *Proc. Natl. Acad. Sci. U.S.A.* 89: 9146); NSE promoter specific for small-cell lung cancer cells (Forss-Petter et al., (1990) *Neuron* 5: 187); somatostatin receptor promoter specific for small cell lung cancer cells (Bombardieri et al., (1995) *Eur. J. Cancer* 31A: 184; Koh et al., (1995) *Int. J. Cancer* 60: 843); c-erbB-3 and c-erbB-2 promoters are specific for breast cancer cells (Quin et al., (1994) *Histopathology* 25: 247); c-erbB4 promoter specific for breast and gastric cancer cells (Rajkumar et al., (1994) *Breast Cancer Res. Trends* 29: 3); thyroglobulin promoter specific for thyroid carcinoma cells (Mariotti et al., (1995) *J. Clin. Endocrinol. Meth.* 80: 468); α-fetoprotein promoter specific for hepatoma cells (Zuibel et al., (1995) *J. Cell. Phys.* 162: 36); villin promoter specific for gastric cancer cells (Osborn et al., (1988) *Virchows Arch. A. Pathol. Anat. Histopathol.* 413: 303); and albumin promoter specific for hepatoma cells (Huber, (1991) *Proc. Natl. Acad. Sci. U.S.A.* 88: 8099).

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

ABBREVIATIONS

SEAP, Secreted Embryonic Alkaline Phosphatase; MRI, magnetic resonance imaging; SPECT, Single-photon emission computed tomography; MC, mini-circle; PP, parental plasmid; WPRE, Woodchuck Hepatitis Virus (WHP) Post-transcriptional Regulatory Element (WPRE; Luc, luciferase; BLI, bioluminescence imaging; ROI, region of interest; AUC, area under the curve; RG, reporter gene; TS, tumor-specific; Fluc (FLUC), firefly luciferase.

DESCRIPTION

Early detection of cancer can dramatically improve the efficacy of available treatment strategies. Yet, despite decades of effort on blood-based biomarker cancer detection, many promising endogenous biomarkers have failed clinically due to intractable problems such as highly variable background expression from non-malignant tissues. Strategies for improved cancer diagnosis have traditionally relied on measurement of endogenous molecules that are over-expressed in cancer cells either via molecular imaging or blood-based assays. A challenge of these strategies is often significant expression within non-cancerous tissues, leading to high background levels and confounding results. An alternative strategy is to utilize promoters of tumor-specific (TS) proteins in exogenously-delivered gene vectors in order to drive the expression of unique reporter genes (RGs) strictly within tumors. For this strategy to become a reality, safety, specificity, and sensitivity are of utmost importance. While safer than viral vectors, two drawbacks of non-viral vectors have been low gene transfer rates and transient expression profiles. Minicircles (MCs) are plasmids that lack a bacterial backbone and are advantageous to overcome the above key issues.

The present disclosure provides embodiments of an alternative and advantageous detection strategy based on systemic administration of safe, tumor-activatable minicircles that utilize the pan-tumor-specific Survivin promoter to drive expression of a secretable reporter gene that is detectable in the blood near-exclusively in tumor-bearing subjects. After systemic administration a robust ability to differentiate mice bearing experimental human melanoma metastases from tumor-free subjects for up to 2 weeks simply by measuring blood reporter levels has been shown. Cumulative changes in reporter levels also identified tumor-bearing subjects, and a receiver operator-characteristic curve analysis highlighted this test's performance with an AUC of 0.918±0.084. Lung tumor burden correlated ($r^2=0.714$; $p<0.05$) with cumulative reporter levels indicating that a determination of disease extent was possible. Continued development of our system could dramatically improve tumor detectability due to temporally-controlled, high reporter expression in tumors and near-zero background from healthy tissues is possible.

Tumor-specific minicircle vectors driving the expression of either secreted embryonic alkaline phosphatase (SEAP) or firefly luciferase (FLUC) have been developed and their utility validated for detecting tumors after systemic administration using blood- and/or imaging-based assays. For gene vectors to be used for cancer screening purposes, challenges include efficient tumor delivery, achieving potent expression for maximum sensitivity, stringent control of expression to attain tumor specificity, and minimization of safety concerns. Tumor-specific minicircle vectors can overcome all of these challenges and it is now shown that systemically administered tumor-specific minicircle vectors can be assayed via serum and non-invasive imaging to differentially identify tumor-bearing subjects from normal subjects. Importantly, the tumor-specific minicircle vectors of the disclosure advantageously have broad applicability in many patient populations since the Survivin promoter drives expression across many different tumor types of tumor cell. The tumor-specific minicircle vectors of the disclosure provide a novel cancer management paradigm that involves tumor detection via an initial blood-based assay, tumor localization via molecular-genetic imaging, and tumor treatment using theranostic tumor-specific minicircle vectors.

The present disclosure encompasses embodiments of nucleic acid minicircle vectors most advantageous for the detection of tumor cells. In particular, the minicircles of the disclosure incorporate a tumor-specific promoter operably linked to a nucleotide sequence desired to be selectively expressed in a tumor cell or a tissue comprising a population of tumor cells. In some embodiments of the disclosure, the minicircle vectors comprise a tumor-specific promoter operably linked to a nucleotide sequence encoding a polypeptide useful as a reporter. Accordingly, when expressed by a recipient tumor cell, the reporter may be detectable, thereby providing information such as a visual image of the tumor cell and/or its location in a tissue of the subject human or non-human animal.

It is contemplated that the minicircle vectors of the disclosure can advantageously deliver an expressible reporter gene to a tumor cell. It is within the scope of the disclosure for the reporter gene to be detectable by such non-invasive detection methods as MRI imaging, PET imaging, SPECT imaging, luminescence imaging and the like. For example, but not intended to be limiting, MRI reporter genes encode for creatine kinase; tyrosinase; transferrin receptor; ferritin; Mag A. PET imaging reporter genes include, but are not limited to such as Herpes simplex virus 1 thymidine kinase (HSV1-TK); hypoxanthine phosphoribosyl transferase; L-amino acid decarboxylase; dopamine 2 receptor (D2R, including the mutant D2RA80); somatostatin receptor; estrogen receptor (hERL); dopamine transporter; sodium iodide symporter; catecholamine transporter; β-galactosidase. PET/SPECT imaging reporter genes include, but are not limited to, Herpes simplex virus Type 1 thymidine kinase and multiple optimized mutants, such as HSV1-sr39tk; dopamine type 2 receptor; sodium iodide symporter; somatostatin type 2 receptor; human norepinephrine transporter; human estrogen receptor α; mutants of human deoxycytidine kinase; and recombinant carcinoembryonic antigen. Bioluminescence reporter genes include, but are not limited to, firefly luciferase (fl); synthetic *Renilla* luciferase (hrl); Enhanced Green Fluorescence protein (egfp); Red Fluorescence Protein (rfp); monomeric Red Fluorescence Protein (mrfp1), and the like. It is further possible for the reporter genes suitable for incorporation into the minicircles of the disclosure to provide multi-modality methods of imaging. For example, but not intended to be limiting, a reporter gene suitable for photoacoustic, MRI, and PET imaging, is the gene encoding human tyrosinase, as described by Qin et al., (2013), *Sci. Rpts.* 3: Art. No.: 1490, incorporated herein by reference its entirety.

In addition to the advantageous use of the minicircles of the disclosure for selectively detecting a recipient tumor cell, the nucleotide sequence operably linked to the tumor-specific promoter may encode a polypeptide useful for modulating the proliferation or metabolic activity of a recipient tumor cell for the purpose of reducing or eliminating the targeted tumor cell from the subject human or non-human animal.

For example, but not intended to be limiting, therapeutically effective polypeptides that are advantageous for targeting and therapeutically challenging a tumor cell include HSVtk; cytosine deaminase; DT diaphorase; nitroreductase; guanine phosphoribosyl transferase; purine nucleoside phosphorylase; thymidine phorphorylase; carboxylesterase; folylpolyglutamyl synthetase; carboxypeptidase A1; carboxypeptidase G2; cytochrome P-450 (CYP2B1), and the like. The activities of these polypeptides for the conversion of a prodrug to an effective therapeutic composition are described in, for example, Harrington et al., (2002) *Clinical Oncology* 14: 148-169 incorporated herein by reference in its entirety.

In further embodiments of the disclosure, it is contemplated that the nucleotide sequence tumor-specifically expressed from the minicircle may not be translated into a heterologous polypeptide but rather may be expressed as a short interfering ribonucleotide sequence (siRNA) that may interact with at least one gene regulatory element of the recipient tumor cell, again modulating the proliferation or metabolic activity of a recipient tumor cell.

Accordingly, it is contemplated to be within the scope of the disclosure to provide embodiments of nucleic acid minicircle vectors (and the parental plasmids thereof) useful for selectively targeting tumor cells cultured in vitro or, most advantageously, in vivo to obtain detectable signals identifying and/or locating a cancerous cell or population of tumor cells in the subject as well as for delivering a therapeutic agent (peptide, polypeptide, nucleic acid) to the targeted tumor cells.

Figure 3:
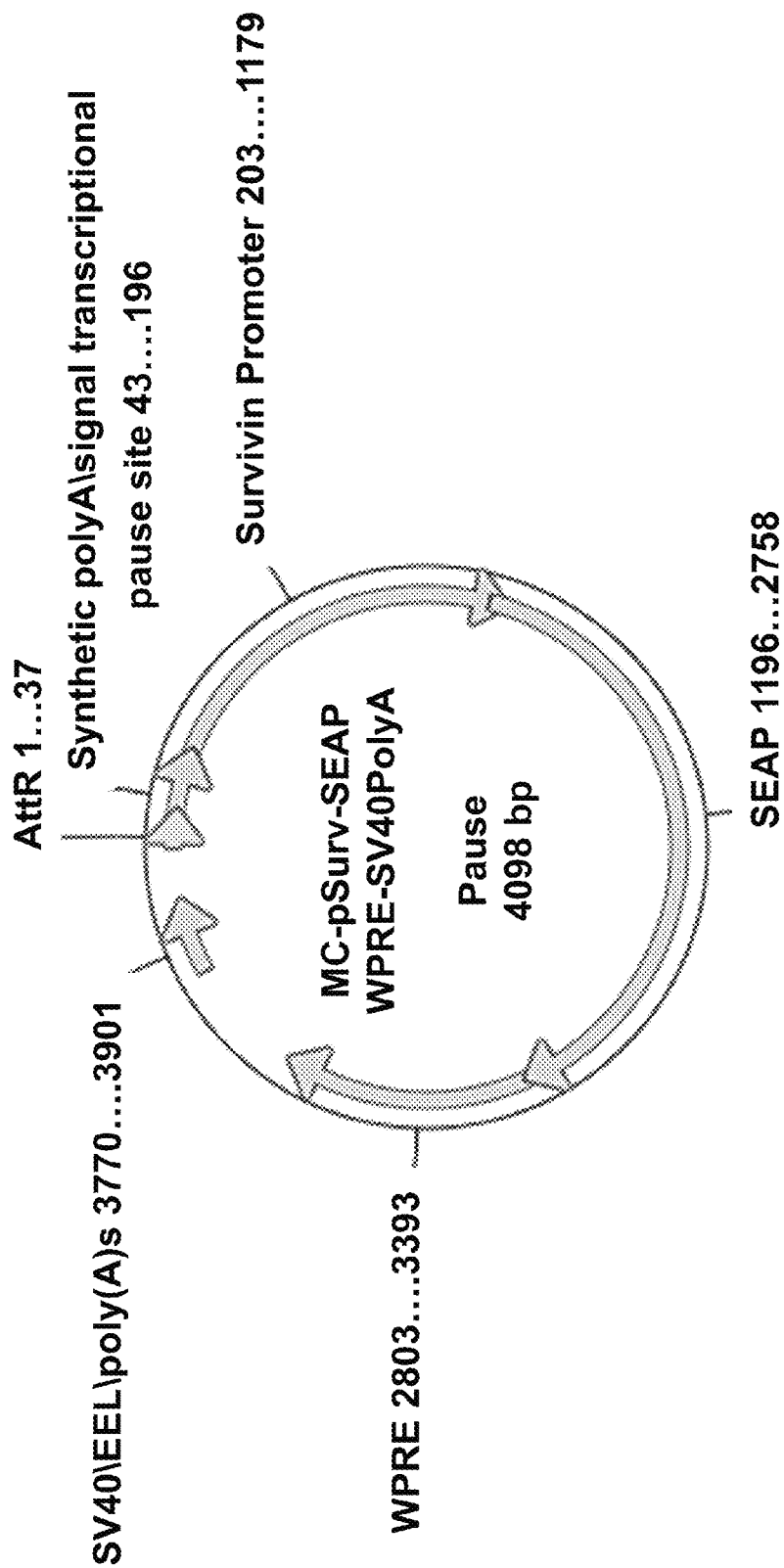
FIG. 3 is a schematic map of minicircle vector construct MC-pSurv-SEAP-WPRE-SV40PolyA-pause.

The present disclosure provides nucleic acid minicircle vectors useful for administering to a subject human or non-human animal for the purpose of detecting the presence of a targeted tumor cell or cells (including a tumor tissue). For example, the minicircle construct MC-pSurv-SEAP-WPRE-SV40PolyA as shown in FIG. 3, and having the nucleotide sequence SEQ ID NO: 1 as shown in FIG. 13, comprises a nucleic acid fragment encoding the detectable polypeptide secreted embryonic alkaline phosphatase (SEAP) operably linked to the tumor-specific promoter pSurvivin.

Figure 4:
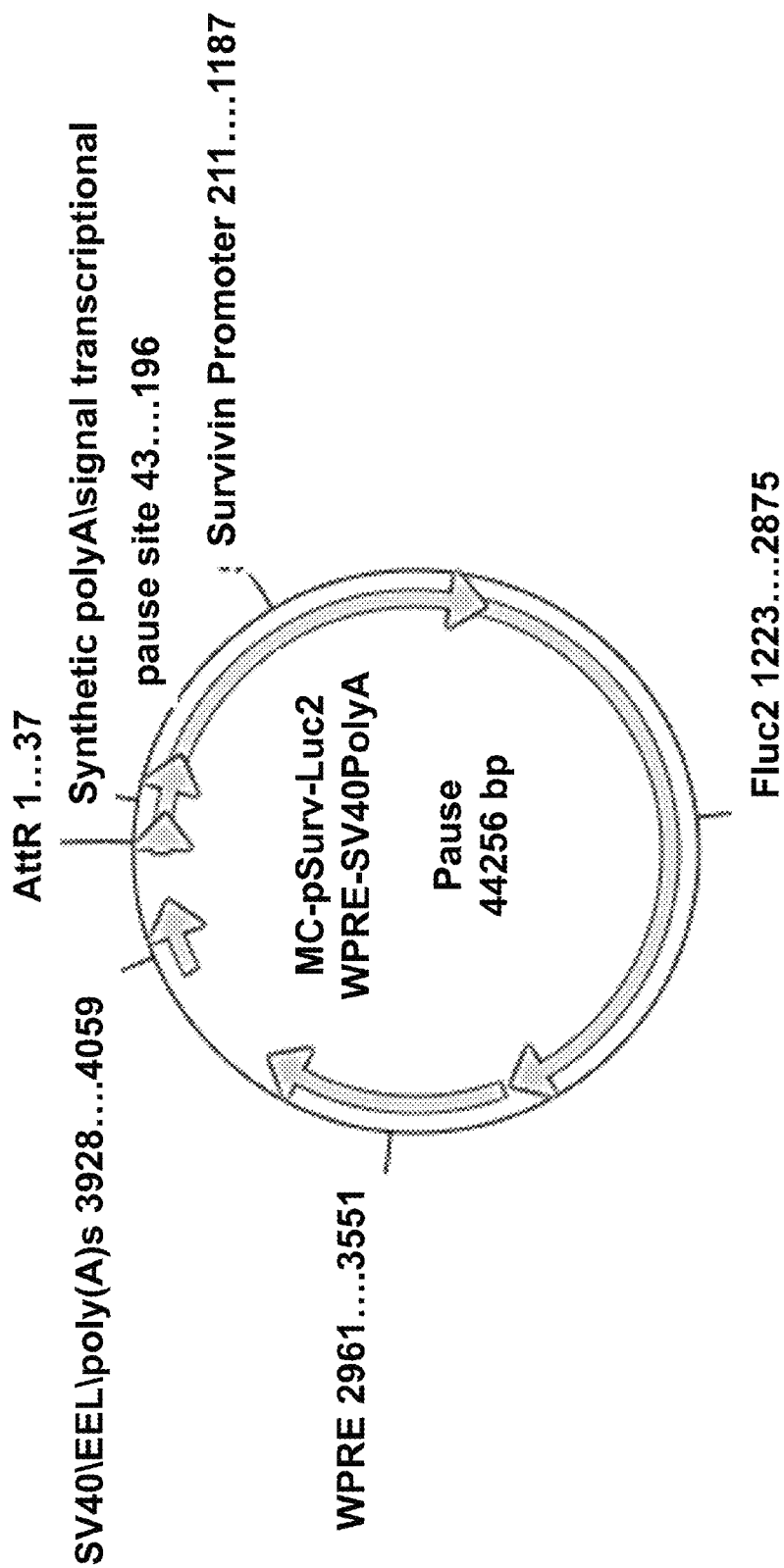
FIG. 4 is a schematic map of minicircle vector construct MC-pSurv-Luc2-WPRE-SV40PolyA-pause.
Figure 5:
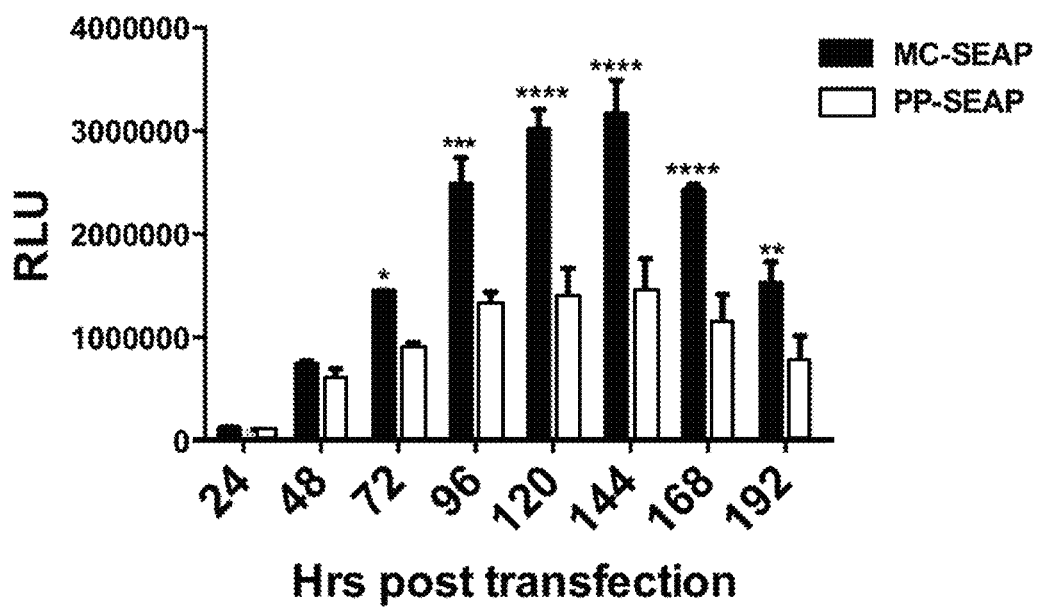
FIG. 5 is a graph illustrating a comparison of tumor-specific plasmids (PP-SEAP) and minicircles (MC-SEAP) in MeWo human melanoma cancer cells.
Figure 6:
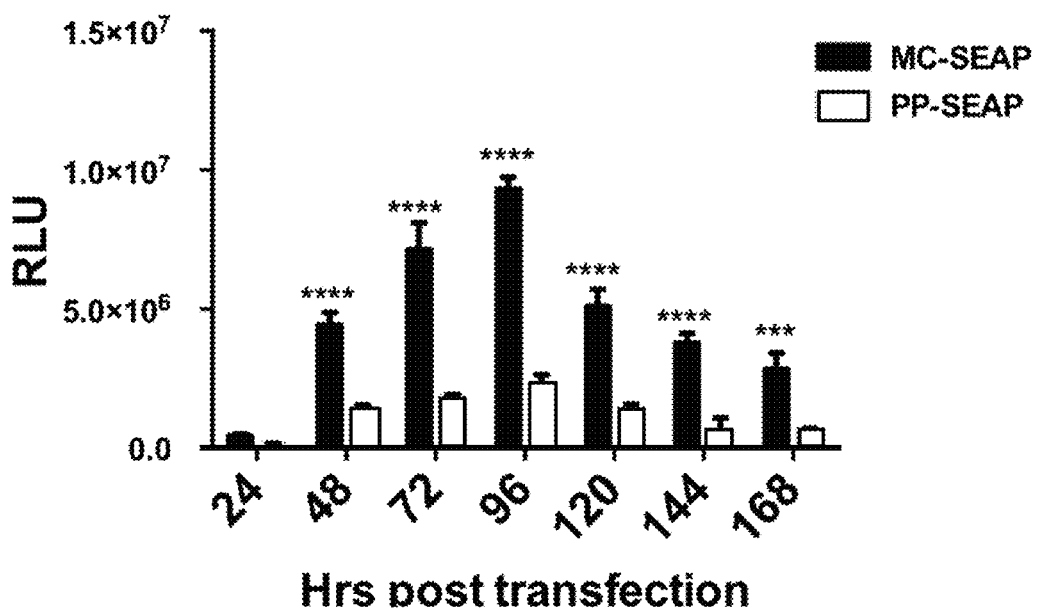
FIG. 6 is a graph illustrating a comparison of tumor-specific plasmids (PP-SEAP) and minicircles (MC-SEAP) in SK-MEL-28 human melanoma cancer cells.

When delivered to cultured melanoma cells, to subcutaneous melanoma xenografts, or intravenously to animals that have a developed tumor, the minicircle vectors of the disclosure provide detectable signals, either as a serum secreted alkaline phosphatase polypeptide or as a bioluminescent signal in the minicircle vector construct where SEAP had been replaced by a luciferase reporter, as shown in FIG. 4 (and having the nucleotide sequence SEQ ID NO: 2 as shown in FIG. 14). Accordingly, it has been demonstrated that the minicircle constructs of the disclosure can identify, in the recipient animal or human, both metastatic tumor cells or a localized tumor.

The present disclosure further provides methods of modulating the physiology or proliferation of a targeted tumor cell by delivering a minicircle nucleic acid to said tumor cell, allowing the targeted cell to express the nucleotide sequence from the nucleic acid sequence operably linked to the tumor-specific promoter, and allowing the expressed product to interact with the targeted cell, thereby modifying the physiological status of the cell or cells.

In a first instance, the disclosure provides embodiments of nucleic acid minicircles wherein a tumor-specific promoter is such as, but not limited to, the Survivin promoter.

Accordingly, to overcome the limitations of endogenous biomarker detection, the disclosure provides embodiments of a strategy based on identification of tumor-bearing individuals using blood-based detection of exogenously delivered genetically-encoded reporters, which produce tumor-driven biomarkers. The main advantage of this strategy is the ability to tailor biomarker expression exclusively in cells of a particular phenotype (i.e. tumor cells), thereby reducing the number of false positives due to protein production from non-malignant tissues. Thus, systemic administration of a tumor-activatable vector encoding a secretable reporter gene can be utilized to identify tumor-bearing subjects provided that transgene expression was transcriptionally targeted to cancer cells using a tumor-specific promoter (a promoter of a gene expressing a protein that is only present in tumors), as shown in FIG. 1. For this strategy to be translated into the clinic, the safety, specificity, sensitivity, and broad applicability are important and each component of the systems of the disclosure were chosen to offer maximum translational potential. Specifically, the present disclosure provides non-viral tumor-activatable minicircles (MCs) encoding a reporter gene including, but not limited to, human secreted embryonic alkaline phosphatase (SEAP) that attain tumor specificity through the use of a tumor-specific promoter such as, but not limited to, the Survivin promoter (pSurv).

While safer than viral vectors, two drawbacks of traditional non-viral vectors (i.e. plasmids) are low gene transfer rates and transient expression profiles. MCs are essentially plasmids that lack the prokaryotic backbone required only for expansion in bacteria. MCs have repeatedly shown to demonstrate improved expression profiles (months in non-dividing, and weeks in dividing, cells) compared to their plasmid counterparts due to their smaller size and reduced promoter silencing (Darquet et al., (1997) *Gene Therapy* 4: 1341-1349; Darquet et al., (1999) *Gene Therapy* 6: 209-218; Chen et al., (2003) *Mol. Therapy: J. Am. Soc. Gene Therapy* 8: 495-500; Chen et al., (2004) *Gene Therapy* 11: 856-864). MCs also conform to regulatory "plasmids free of antibiotic resistance genes" (pFAR) principles (Marie et al., (2010) *J. Gene Med.* 12: 323-332). Moreover, while producing MCs was traditionally very labor-intensive and time-consuming, more recent advances in MC production schemes have made it possible to produce large quantities in short periods of time with relative ease and reduced costs (Kay et al., (2010)

Nat. Biotech. 28: 1287-1289). Finally, while integration is a safety concern with many gene (particularly viral) vectors, even with effective in vivo delivery methods like direct local injection and electroporation, the integration rates of non-viral vectors are approximately 1-3 orders of magnitude below the rate of spontaneous gene-inactivating mutations (Wang et al., (2004) *Gene Therapy* 11: 711-721; Nichols et al., (1995) *Annals New York Acad. Sci.* 772: 30-39; Ledwith et al., (2000) *Develop. Biologicals* 104: 33-43; Ledwith et al., (2000) *Intervirology* 43: 258-272). Hence, MCs have become one of the most useful non-viral vector platforms in terms of translational potential, potency and safety.

SEAP is the most commonly used secretable reporter protein and has many ideal characteristics. It is an artificial, C-terminal truncated, secretable form of human placental alkaline phosphatase (PLAP) that is only expressed during embryogenesis; thus it is a unique reporter not normally found in the blood and should have near-zero background (Berger et al., (1988) *Gene* 66: 1-10). Compared to PLAP, SEAP is unusually heat-stable; thus heating samples to 65° C. allows SEAP to be specifically assayed (Bronstein et al., (1994) *BioTechniques* 17: 172-174, 76-177). Commercial SEAP detection assays are extremely sensitive over at least a 4-log order concentration range, with detection limits in the picogram/ml range. SEAP is also an advantageous protein-based reporter for translation into the clinic since: 1) it has shown effective longitudinal monitoring of non-viral gene transfer in mice and large animals (Brown et al., (2008) *Methods Mol. Biol.* 423: 215-224); 2) its human origin implies it can have reduced or zero immunogenic potential in patients similar to what has been shown with murine SEAP (muSEAP) in immunocompetent mice (Wang et al., (2001) *Gene* 279: 99-108); and 3) SEAP has been used in the clinic to monitor antibody levels following administration of an HPV16/18 AS04-adjuvanted vaccine (Kemp et al., (2008) *Vaccine* 26: 3608-3616).

The systems of the disclosure utilize pSurv to drive the expression of SEAP. Survivin is a member of the apoptosis inhibitor family that helps control mitotic progression and prevent cell death and is over-expressed in many cancers such as melanoma, liver, lung, breast, colon and ovarian, but not in healthy adult tissues (Ito et al., (2000) *Hepatology* 31: 1080-1085; Chen et al., (2004) *Cancer Gene Therapy* 11: 740-747; Lu et al., (2005) *Gene Therapy* 12: 330-338). pSurv, therefore, is advantageous for transcriptional targeting of tumors as demonstrated in models of lung, melanoma, colon, breast, ovarian, and liver cancer (Lu et al., (2005) *Gene Therapy* 12: 330-338; Li et al., (2006) *J. Gene Med.* 8: 1232-1242; van Houdt et al., (2006) *J. Neurosurgery* 104: 583-592; Ahn et al., (2011) *Gene Therapy* 18: 606-612; Ray et al., (2008) *Mol. Therapy: J. Am. Soc. Gene Therapy* 16: 1848-1856). Thus, the tumor-specific promoter-driven tumor-activatable MCs of the disclosure offer broad applicability for effective cancer screening across numerous tumor types and patient populations.

Accordingly, diagnostic tumor-activatable MCs have been developed and tested for the ability to distinguish tumor-bearing subjects from healthy subjects after systemic administration of the MCs by measuring blood levels of a genetically-encoded cancer biomarker. For delivery, the MCs were compared with a non-targeted transfection agent that has been shown to have no immunogenicity (Bonnet et al., (2008) *Pharmaceut. Res.* 25: 2972-2982), the ability to repeatedly dose animals, and the ability efficiently transfect both primary and metastatic tumors in mice after systemic (tail-vein) administration (Yang et al., (2013) *Proc. Nat. Acad. Sci. U.S.A.* 110: 14717-14722; Bhang et al., (2011) *Nat. Med.* 17: 123-129). The results indicate that use of tumor-activatable MCs is an advantageous promising platform technology for safe and efficacious cancer screening. This system is useful for monitoring patients at high-risk for tumor recurrence, followed by screening high-risk populations prior to tumor diagnosis, and can be advantageous for screening for the general population.

An exogenously delivered genetically-encoded cancer blood biomarker vector strategy according to the disclosure can overcome some of the inherent limitations of cancer screening targeting endogenous cancer blood biomarkers such as high background expression in healthy tissues and random fluctuations in biomarker expression over time. The present disclosure provides embodiments of a tumor-activatable MC system that can be administered systemically to identify tumor-bearing subjects using a simple and relatively inexpensive blood-based assay. The assay showed reliable detection capabilities and assessment of disease extent, indicating the feasibility of tumor-activatable MCs as a highly robust and safe cancer screening system.

Desirable cancer gene therapy will express a therapeutic transgene specifically within a tumor so that healthy cells are not harmed. To reach this goal several strategies have been explored including transcriptional targeting of tumors using tumor-specific promoters (Ahn et al., (2011) *Gene Therapy* 18: 606-612; Ye et al., (2003) *Biochem. Biophys. Res. Comms.* 307: 759-764; Iyer et al., (2005) *Transgenic Res.* 14: 47-55), transcriptional de-targeting of healthy tissues using endogenous miRNA regulation (Cawood et al., (2009) *PLoS Pathogens* 5: e1000440; Ronald et al., (2013) *Gene Therapy* 20: 1006-1013), enhanced tumor tropism of both viral (transductional targeting) and non-viral vectors (Chisholm et al., (2009) *Cancer Res.* 69: 2655-2662; Bachtarzi et al., (2008) *Expert Opinion Drug Delivery* 5: 1231-1240), or combinations of these strategies (Tsuruta et al., (2008) *Clin. Cancer Res.* 14: 3582-3588; Sugio et al., (2011) *Clin. Cancer Res* 17: 2807-2818). The systems of the disclosure provide a means of expressing a secretable reporter gene for the purposes of cancer detection. With this application of gene vectors comes the additional challenge of overcoming heightened safety concerns, since as a potential screening tool the vectors could be used in patients without any clearly visible evidence of cancer. Therefore, all components of this type of system need to be safe including the delivery vehicle (if needed), the DNA vector itself, and the transgene (if expressed).

While many delivery formulations are known in the art and contemplated for use with the MC systems of the disclosure, an in vivo transfection agent that has a desirable safety profile (i.e. no immunostimulation) (Bonnet et al., (2008) *Pharmaceut. Res.* 25: 2972-2982), and is in phase I/I clinical trials (Lisziewicz et al., (2012) *PLoS ONE* 7:e35416) was particularly preferred. Furthermore, while non-viral vectors are much safer than viral vectors (i.e. low/nearly zero integration rates, lowered immunogenic potential), there is still a concern regarding immunostimulatory prokaryotic CpG motifs in the backbone of traditional plasmids. This concern is alleviated in MCs since these vectors lack a prokaryotic backbone. SEAP was selected since it is of human origin so it should not cause an immunogenic reaction (Wang et al., (2001) *Gene* 279: 99-108), and has already shown promise in the clinic (Kemp et al., (2008) *Vaccine* 26: 3608-3616).

The tumor-activatable transgene expression systems of the present disclosure were developed by generating MCs utilizing a pan-tumor-specific promoter. Although one other tumor-activatable MC system, MC-oriP-IFNγ, has been described (Zuo et al., (2011) *PLoS ONE* 6: e19407) it uses the oriP promoter to drive interferon-γ expression in Epstein-Barr virus (EBV) infected nasopharyngeal carcinomas (NPC). In contrast, the MC systems of the disclosure can be broadly applicable for many different tumor types. The non-viral MC vectors of the present disclosure were developed for use in cancer screening using a blood-based assay.

Although tumor-activatable reporter gene-expressing vectors for cancer detection have been developed (Bhang et al., (2011) *Nat. Med.* 17: 123-129; Chaudhuri et al., (2003) *Technol. In Cancer Res. & Treat.* 2: 171-180; Warram et al., (2011) *Mol. Imaging Biol.* 13: 452-461; Warram et al., (2012) *Cancer Gene Therapy* 19: 545-552; Browne et al., (2011) *PLoS ONE* 6: e19530). The vector systems used in these cases (adenoviruses, Herpes simplex viruses, and plasmids), however, have safety issues that hamper clinical translation. Viruses are highly immunogenic and pre-existing viral immunity in humans is a widespread problem (Browne et al., (2011) *PLoS ONE* 6: e19530; Sumida et al., (2005) *J. Immunol.* 174: 7179-7185; Schirmbeck et al., (2008) *Mol. Therapy* 16: 1609-1616). Plasmids are also immunogenic due to unmethylated CpG sequences in the prokaryotic backbone (necessary only for plasmid production) (Tan et al., (1999) *Human Gene Therapy* 10: 2153-2161), as well as typically bearing coded antibiotic resistance genes to endogenous flora (Marie et al., (2010) *J. Gene Med.* 12: 323-332). Thus the tumor-activatable MCs of the present disclosure have advantages over these other vectors and offer translational potential primarily due to easier manufacturing practices (compared to viruses) and a more desirable profile.

The MC systems of the disclosure can provide improved specificity through two mechanisms: 1) the uniqueness of the biomarker in the blood since no SEAP is detectable prior to MC administration; and 2) the ability to drive expression strictly within the tumor, thereby alleviating signal in healthy tumor-free subjects. A slight SEAP signal from tumor-free mice receiving MC likely is from leakiness of pSurv. It is contemplated, however, that the MC systems of the disclosure are not limited to this particular promoter and alternative tumor-activatable promoters such as, but not limited to, the Id1 or hTERT promoters (Warram et al., (2011) *Mol. Imaging Biol.* 13: 452-461; Zhang et al., (2008) *Life sciences* 82: 1154-1161) and the like are useful in the MCs of the disclosure. Also, sensitivity using endogenous biomarkers is inherently limited by the amount of biomarker produced by the tumor (Hori & Gambhir (2011) *Sci. Translational Med.* 3: 109ra116). In contrast, the sensitivity of the MC systems of the disclosure can be modified.

One of the advantages of endogenous blood biomarkers is that they can be used to determine what type of cancer a person may harbor (e.g. a high PSA level may indicate prostate cancer). However, the MC systems provided by the present disclosure are also advantageous for screening for all cancer, not a particular tumor type. It is further contemplated that alternative promoters useful for screening patients at high-risk for a particular cancer, such as variants of the prostate-specific antigen enhancer/promoter for prostate cancer (Iyer et al., (2005) *Transgenic Res.* 14: 47-55; Iyer et al., (2004) *Mol. Therapy* 10: 545-552; Iyer et al., (2006) *Human Gene Therapy* 17: 125-132) or the mucin-1 promoter for breast cancer (Huyn et al., (2009) *Clin. Cancer Res.* 15: 3126-3134) and the like can be incorporated into the MC systems of the disclosure.

Another limitation of exogenous biomarkers (i.e. reporter) is the inability to localize the site(s) in the body where the biomarker originated. By replacing or co-expressing SEAP with an imaging reporter gene (e.g., herpes simplex virus thymidine kinase 1 for positron emission tomography (PET)) the systems of the disclosure can also allow tumor location to be visualized. Bhang et al. recently described the ability to image tumors using both BLI and single photon emission computed tomography (SPECT) following systemic administration of tumor-activatable plasmids expressing the appropriate imaging reporter gene (Bhang et al., (2011) *Nat. Med.* 17: 123-129). This strategy was also pursued with the SEAP-expressing viral vectors described to date since these vectors co-expressed fluorescent proteins for cancer visualization using fluorescence stereomicroscopy (Chaudhuri et al., (2003) *Technol. In Cancer Res. & Treat.* 2: 171-180; Warram et al., (2011) *Mol. Imaging Biol.* 13: 452-461; Warram et al., (2012) *Cancer Gene Therapy* 19: 545-552). Rather than one vector system expressing two reporters. It is further contemplated to be possible to deliver two different vectors designed for specific applications; one for cancer screening expressing a secretable reporter, and one for tumor localization expressing an imaging reporter.

One aspect of the disclosure, therefore, encompasses embodiments of a recombinant nucleic acid minicircle vector comprising a nucleotide sequence operably linked to a tumor-specific gene expression promoter and expressible at a level greater by a recipient tumor cell than by a non-tumor cell.

In the embodiments of this aspect of the disclosure the tumor-specific gene expression promoter may be selected from the group consisting of: a survivin promoter, a CXCR4 promoter, a Hexokinase type II promoter, a TRPM4 (Transient Receptor Potential-Melastatin 4) promoter, a stromelysin 3 promoter, a surfactant protein A promoter, a secretory leukoprotease inhibitor (SLPI) promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein (DF3, MUC1) promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter; a villin promoter, and an albumin promoter.

In some embodiments of this aspect of the disclosure, the nucleotide sequence operably linked to the tumor-specific promoter can be expressed as a polypeptide.

In some embodiments of this aspect of the disclosure, the nucleotide sequence operably linked to the tumor-specific promoter can encode a reporter polypeptide.

In some embodiments of this aspect of the disclosure, the reporter polypeptide may be an MRI reporter, a PET reporter; a SPECT reporter, a photoacoustic reporter, a bioluminescent reporter, or any combination thereof.

In some embodiments of this aspect of the disclosure, the polypeptide can be secreted embryonic alkaline phosphatase (SEAP).

In some embodiments of this aspect of the disclosure, the recombinant nucleic acid minicircle vector can have the nucleic acid sequence according to SEQ ID NO: 1.

In some embodiments of this aspect of the disclosure, the polypeptide can be a bioluminescent reporter.

In some embodiments of this aspect of the disclosure, the recombinant nucleic acid minicircle vector can have the nucleic acid sequence according to SEQ ID NO: 2.

In some embodiments of this aspect of the disclosure, the nucleotide sequence operably linked to the tumor-specific promoter can be expressed as a small interfering RNA (siRNA) or a therapeutically effective polypeptide.

Another aspect of the disclosure encompasses embodiments of a pharmaceutically acceptable composition comprising a recombinant nucleic acid minicircle vector comprising a nucleotide sequence operably linked to a tumor-specific gene expression promoter and expressible at a level greater by a recipient tumor cell than by a non-tumor cell, and a pharmaceutically acceptable carrier, wherein: (i) the tumor-specific gene expression promoter can be selected from the group consisting of: a survivin promoter, a CXCR4 promoter, a Hexokinase type II promoter, a TRPM4 (Transient Receptor Potential-Melastatin 4) promoter, a stromelysin 3 promoter, a surfactant protein A promoter, a secretory leukoprotease inhibitor (SLPI) promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein (DF3, MUC1) promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter; and villin promoter, and an albumin promoter; and (ii) the nucleotide sequence operably linked to the tumor-specific promoter can be expressed as a polypeptide encoding an MRI reporter, a PET reporter, a SPECT reporter, a photoacoustic reporter, a bioluminescent reporter, or any combination thereof.

In some embodiments of this aspect of the disclosure, the recombinant nucleic acid minicircle vector can have the nucleic acid sequence according to SEQ ID NO: 1 or SEQ ID NO: 2.

Yet another aspect of the disclosure encompasses embodiments of a method of detecting a tumor cell in a human or non-human subject, comprising the steps of: (i) delivering to a first subject human or non-human animal a pharmaceutically acceptable composition comprising a recombinant nucleic acid minicircle vector comprising a nucleotide sequence operably linked to a tumor-specific gene expression promoter and expressible at a level greater by a recipient tumor cell than by a non-tumor cell, and a pharmaceutically acceptable carrier, wherein: (a) the tumor-specific gene expression promoter can be selected from the group consisting of: a survivin promoter, a CXCR4 promoter, a Hexokinase type II promoter, a TRPM4 (Transient Receptor Potential-Melastatin 4) promoter, a stromelysin 3 promoter, a surfactant protein A promoter, a secretory leukoprotease inhibitor (SLPI) promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein (DF3, MUC1) promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter; a villin promoter, and an albumin promoter; and (b) the nucleotide sequence operably linked to the tumor-specific promoter can be expressed as a polypeptide encoding an MRI reporter, a PET reporter, a SPECT reporter, a photoacoustic reporter, a bioluminescent reporter, or any combination thereof; and (ii) detecting an expression product in the first subject, wherein said expression product is generated from the nucleotide sequence operably linked to the tumor-specific gene expression promoter of the minicircle vector, and wherein the detection of said expression product indicates the presence of a tumor cell in the first subject In some embodiments of this aspect of the disclosure, the expression product can be a serum polypeptide and step (ii) can comprise obtaining a serum sample from the first subject and determining the serum level of the expression product generated from the minicircle vector.

In some embodiments of this aspect of the disclosure, the detected expression product can be secreted embryonic alkaline phosphatase (SEAP).

In some embodiments of this aspect of the disclosure, the minicircle vector can have the nucleic acid sequence according to SEQ ID NO: 1.

In some embodiments of this aspect of the disclosure, the expression product can be a bioluminescent polypeptide and the step (ii) can comprise generating a detectable signal derived from the expression product, measuring the level of the detectable signal generated from the minicircle vector, and comparing the level of the signal from the first subject to that obtained from a second subject not receiving the minicircle vector, wherein an elevated level signal from the first subject compared to that level obtained from a second subject indicates that the first subject comprises a tumor cell or population of tumor cells.

In some embodiments of this aspect of the disclosure, the step (ii) can further comprise non-invasively detecting the detectable signal, converting said signal into an image, overlaying said image with an image of the first subject, and locating the detectable signal relative to the first subject, thereby determining the position of a tumor cell or population of tumor cells in the first subject.

In some embodiments of this aspect of the disclosure, the expression product can be a luciferase.

In some embodiments of this aspect of the disclosure, the minicircle vector can have the nucleic acid sequence according to SEQ ID NO: 2.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLE

Example 1

Plasmid and Minicircle Construction

All plasmids were constructed using standard PCR and cloning technology and sequenced by Sequetech (Mountain View, Calif.). To generate both parental plasmids (PP) and MCs the system described by Kay et al., (2010) *Nat. Biotechnol.* 28: 1287-1289, incorporated herein by reference in its entirety was used (System Biosciences, Mountain View, Calif.). The 977 base-pair (bp) Survivin promoter was subcloned from pSurv-FL (Ray S, et al. (2008) *Molecular therapy: J. Am. Soc. Gene Therapy* 16:1848-1856) into the MN-100 PP backbone (System Biosciences, Mountain View, Calif.) containing a SV40 polyA and Woodchuck Hepatitis virus posttranscriptional element (WPRE) to generate PP-pSurv-WPRE. Next, the SEAP transgene from pSELECT-zeo-SEAP (Invivogen, San Diego, Calif.) was subcloned into PP-pSurv-WPRE to generate PP-pSurv-SEAP-WPRE (FIG. 2A-top). Both PP-pSurv-SEAP-WPRE (PP) and MC-pSurv-SEAP-WPRE (MC) (FIG. 2A-bottom) were amplified and purified according to the protocol outlined in Kay et al., (2010) *Nat. Biotechnol.* 28: 1287-1289) and the supplier's instructions (System Biosciences, Mountain View, Calif.).

ZYCY10P3S2T *E. coli* were transformed with the PP, colonies were picked and *E. coli* were grown overnight in TB broth. To generate MCs, site-specific recombination via expression of phiC31 integrase was initiated by addition of equal volume of LB broth containing 0.001% L-arabinose and 16 mL NaOH, and cultures were grown for an additional 5.5 h at 30° C. For the PP, the cells were grown in the same media without L-arabinose supplementation. Endotoxin-free mega kits (Qiagen, Valencia, Calif.) were used to purify both PP and MC.

Example 2

Cell Culture and Transfection

MDA-MB-231 (ATCC, Manassas, Va.), MeWo (ATCC, Manassas, Va.) and SK-MEL-28 human melanoma cell lines were maintained on MEM and DMEM (Gibco, Carlsbad, Calif.), respectively. Media was supplemented with 10% Fetal Bovine Serum (FBS) and 1× Antibiotic-Antimycotic solution (Life Technologies) and cells were maintained in 5% $CO_2$ incubator at 37° C.

Cell lines were plated (1.25×10$^5$ cells per well) in 24-well plates 1 day prior to transfection. Cells were transfected with equal mass of PP or MC (1 µg) and 2 µl of a linear polyethylenimine transfection agent (jetPEI, Polyplus transfection, Illkirch, France) according to the manufacturer's instructions. Medium was collected daily, centrifuged at 1200 rpm for 3 min and the supernatant was stored at −20° C. until SEAP concentrations were measured. Following medium collection, each well was washed with PBS and fresh medium was added; therefore SEAP measurements reflect protein production over a 24-h period.

Example 3

Subcutaneous Tumor Model and Intratumoral Administration of Minicircles

2×10$^6$ MeWo cells were implanted into the right flank of female nude mice (Nu/Nu; Charles River) and tumors developed over a period of 3 weeks (n=4). MCs (20 µg) were complexed with a linear polyethylenimine transfection agent (in vivo-jetPEI, Polyplus transfection, Illkirch, France) at an N/P ratio of 6 (N/P is the number of nitrogen residues in in vivo-jetPEI per nucleic acid phosphate) and resuspended in 50 µl 5% glucose.

Intratumoral (I.T.) injections were performed over approximately 2 min by injecting DNA-transfection agent complexes at multiple loci within each tumor. Two cohorts of control mice received either an intramuscular (I.M.) injection of MC at the same dose (n=3) or an I.T. injection of 5% glucose only (n=3).

Example 4

Experimental Melanoma Metastases Model, BLI, and Systemic Administration of Minicircles To evaluate the ability to detect tumors after systemic administration of MCs, an experimental metastases model described previously (Bhang et al., (2011) *Nat. Med.* 17:123-129) was used. 5×10$^6$ MeWo cells stably expressing a BRET fusion protein (RLuc8.6-TurboFP-BRET6) (Dragulescu-Andrasi et al., (2011) *Proc. Nat. Acad. Sci. U.S.A.* 108: 12060-12065) were injected into irradiated (5 Gy) female nude mice (Nu/Nu; Charles River) via the tail-vein (200 µl of PBS total volume). At weekly intervals following cell injection, tumor development was monitored with BLI immediately following intravenous administration of the substrate coelenterazine (35 µg/mouse; diluted in 150 µl of PBS) using an IVIS-200 imaging system (PerkinElmer). Using the software package Living Image 4.1, region of interests (ROIs) were drawn over the lungs in each image to quantitate tumor burden. BLI data is expressed as lung average radiance in photons/second/cm$^2$/steradian.

Tumor-bearing mice (n=7) or irradiated control mice (n=7) were administered 40 µg of MC complexed with a linear polyethylenimine transfection agent (N/P ratio of 8; in vivo-jetPEI, Polyplus transfection, Illkirch, France) and resuspended in 400 µl of 5% glucose. Mice were then injected via the tail-vein with two 200 µl injections and a gap of 5 minutes between the first and second injection. An additional control group (n=5) of irradiated mice were administered 400 µl of 5% glucose alone.

Example 5

Plasma Collection

Blood samples were collected via the submandibular vein at least 1 day prior to MC injection and for up to 2 weeks following injection. Blood (approximately 75-100 ml) was collected in lithium heparin-coated microtubes (BD), kept on ice before processing, and then centrifuged at 10,000×g for 5 min at 4° C. Plasma was collected and stored at −80° C. prior to SEAP measurements.

Example 6

SEAP Assay

To measure SEAP concentration in both medium and plasma the Great EscAPe SEAP Chemiluminescence Assay kit 2.0 according the manufacturer's instructions (Clontech) was used. Briefly, 25 µl of medium or plasma was added to 1× dilution buffer, and endogenous alkaline phosphatase was heat-inactivated at 65° C. for 30 min. Samples were put on ice for 3 min and then allowed to recover to room temperature. 100 µl of SEAP substrate was added, incubated for 30 min at room temperature, and luminescence (relative light units; RLU) was measured over 10 sec using a TD 20/20 luminometer (Turner Designs, Sunnyvale, Calif.).

Example 7

Tumor-Activatable Minicircles are Advantageous Over Plasmids Across Multiple Melanoma Cell Lines The transcriptional activity of two tumor-specific promoters, pSurv and the progression elevated gene-3 promoter (pPEG) (Bhang et al., (2011) *Nat. Med.* 17: 123-129) were compared to assess which promoter would give the lowest background in healthy tissues. Plasmids expressing a codon-optimized firefly luciferase (Luc2) driven by either pSurv or pPEG were constructed and delivered systemically into healthy female Nu/Nu mice. After two days, pSurv-driven plasmids showed significantly lower background Luc2 expression than pPEG driven constructs, particularly in the heart and lung (FIGS. 18A-18D). The tumor-specific promoter activity in both primary human fibroblasts and two human tumor cell lines was also compared. Again, pSurv had lower background activity in human fibroblasts and equivalent or higher expression in tumor cell lines (FIGS. 19A-19C).

Figure 15:
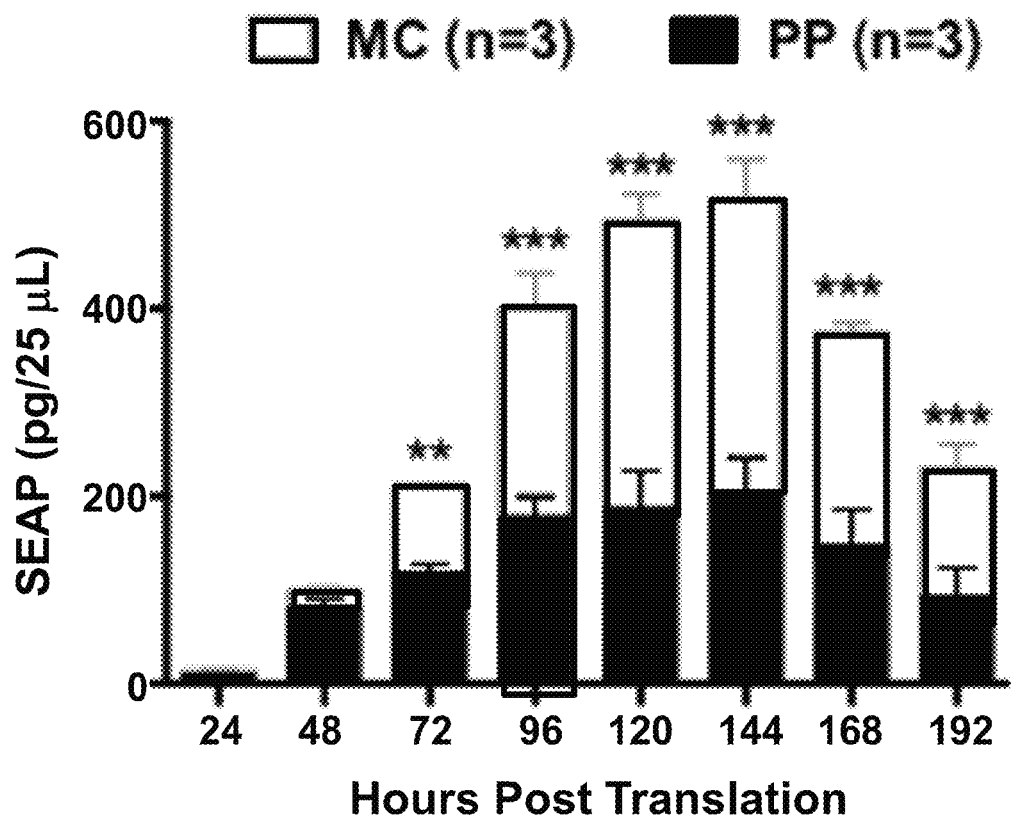
FIG. 15 is a graph illustrating a comparison of the transfections of the constructs of the disclosure in cultured cancer cells. Transfection of equal mass of MC (n=3) and PP (n=3) using equal volumes of transfection agent into MeWo human melanoma cells lead to significantly higher SEAP concentration in medium with MCs from day 3 to day 8 (p<0.01; *p<0.001). Data is expressed as mean±SD
Figure 20:
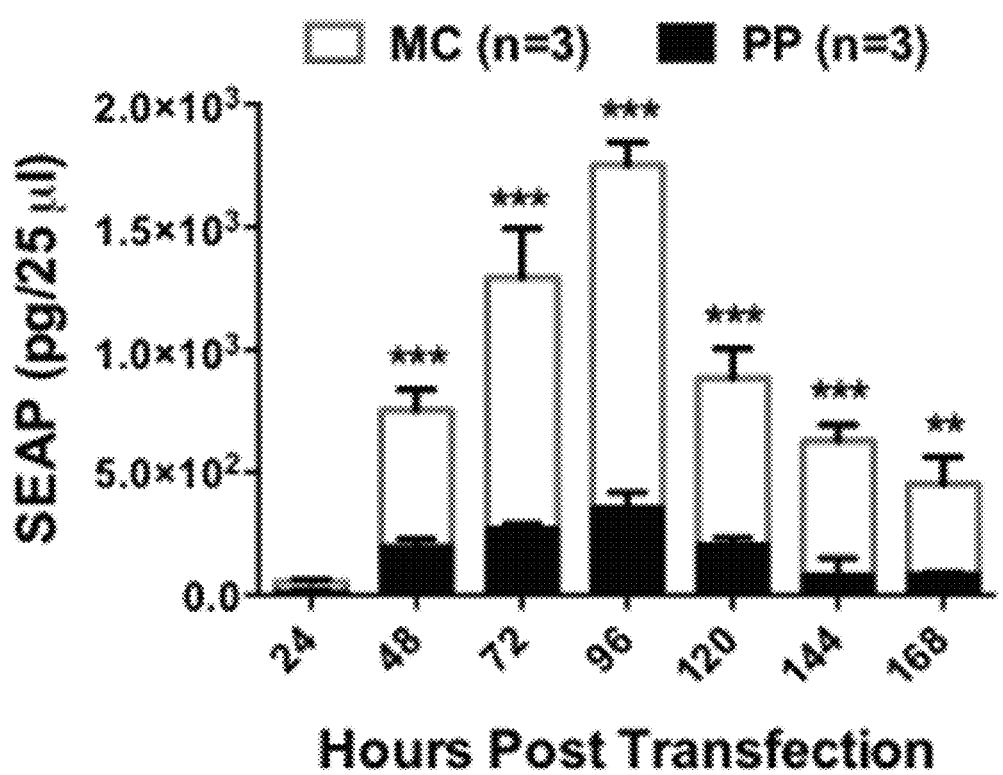
FIG. 20 illustrates a comparison of tumor-activatable PPs and MCs in cultured SK-MEL-28 melanoma cells. SK-MEL-28 human melanoma cells were transfected with equal masses of tumor-activatable MC (n=3) and PP (n=3) and equal volumes of transfection agent PEI. Significantly higher SEAP activity was observed in medium of cells transfected with MCs from 10 day 2 to day 7 ($p<0.01$; $*p<0.001$). Data is expressed as mean±SD.
Figure 21A:
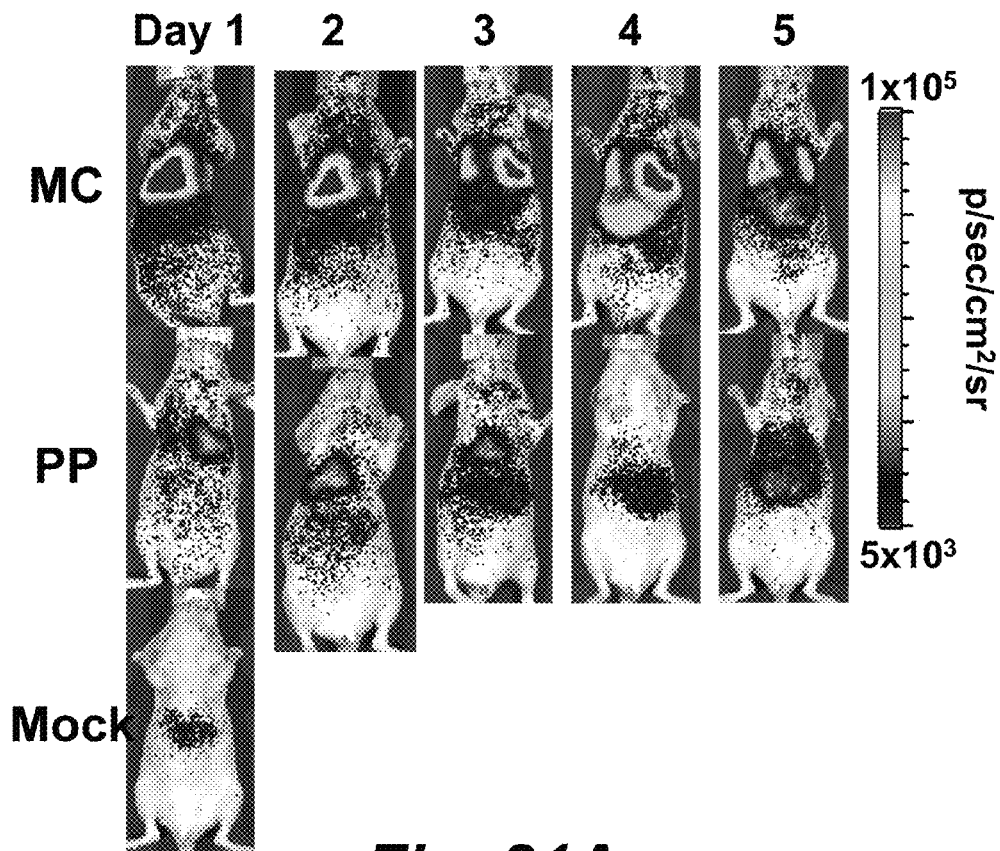
FIGS. 21A and 21B illustrate a comparison of transgene expression between MCs and PPs driven by a strong constitutive promoter in healthy (tumor-free) mice.
Figure 21B:
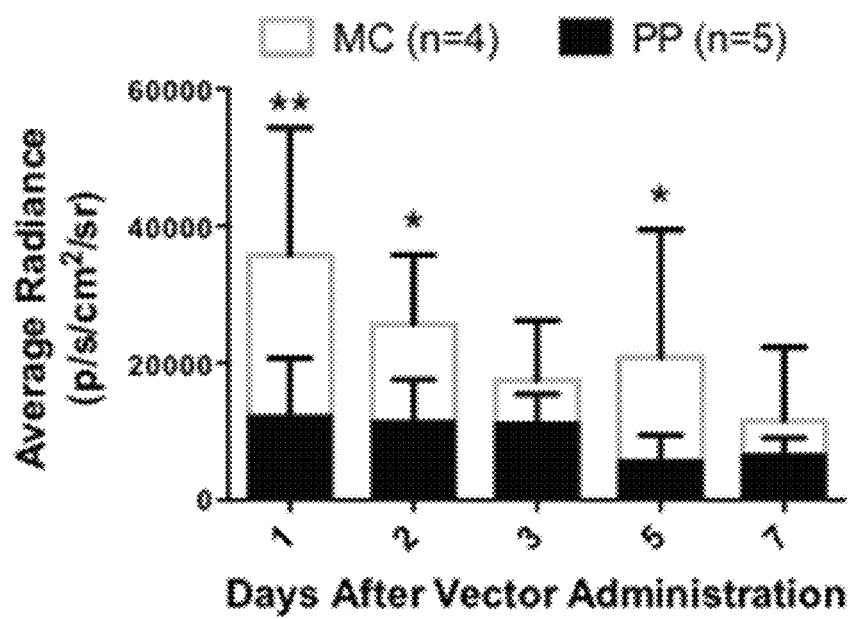

Tumor-activatable parental plasmids (PP; approximately 7.9 kb) and minicircles (MC; approximately 4.1 kb) with pSurv driving SEAP expression (FIGS. 2A-4) were developed. To compare SEAP concentration attainable with these two constructs, two human melanoma cell lines (MeWo, FIG. 15; and SK-MEL-28, FIG. 20) were transfected with equal mass of PP and MC and equal volume of a linear polyethylenimine (PEI) transfection agent. Equal mass was compared since the main advantage of MC usage is their smaller size and the main dose limitation of non-viral DNA vectors in vivo is typically the amount of transfection agent, not the amount of DNA. Following transfection, SEAP concentration was measured in the culture medium each day for up to 8 days. Each data point reflected the SEAP accumulation within the previous 24-hour period not the cumulative SEAP concentration across multiple days. By day 3 in MeWo cells, MCs had significantly higher SEAP concentration in the medium compared to PPs and these differences were maintained until the last day (day 8) of the experiment (FIG. 15). Similar results were obtained for SK-MEL-28 cells. The only significant differences were noted at day 2 (FIG. 20). Therefore, MCs driven by the tumor-activatable pSurv have improved transgene expression profiles in melanoma cancer cells compared to their parental plasmid counterparts. To ensure that MCs provide an advantage over PPs in vivo, the transgene expression levels achieved by PPs and MCs driven by the strong constitutive elongation factor-1 alpha promoter (pEF1) after systemic administration in mice (n=5 for PP and n=4 for MC) were compared and found significantly higher (p<0.05) lung expression with MCs at multiple time points post-delivery (FIGS. 21A and 21B).

Example 8

Figure 7:
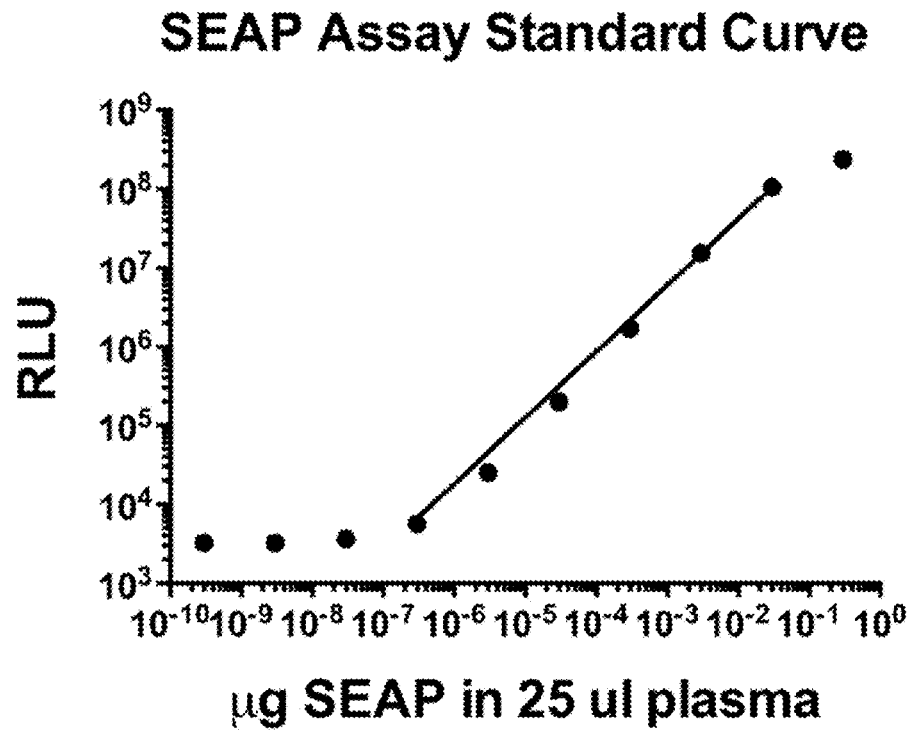
FIG. 7 is a SEAP assay standard curve for blood-based cancer detection after systemic administration of tumor-specific SEAP Minicircles. Standard curve analysis of the SEAP assay revealed that RLU values above approximately $10^4$ were within the linear region of detectable SEAP levels in plasma.
Figure 8:
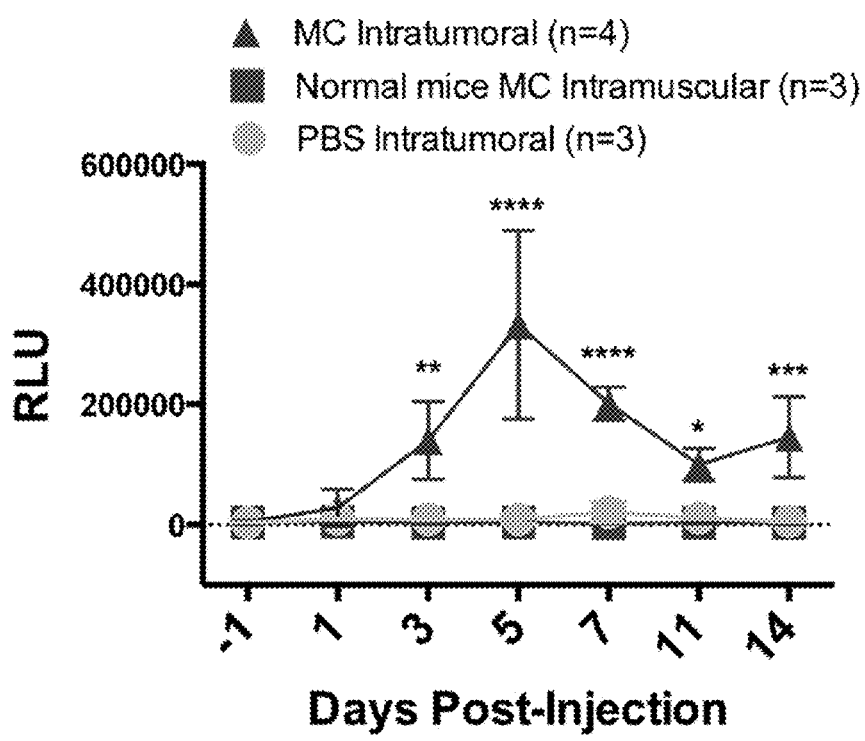
FIG. 8 is a graph illustrating that intratumoral administration of tumor-activatable MCs leads to detectable blood reporter activity. Nude mice bearing subcutaneous human melanoma xenografts were intratumorally (I.T.) administered tumor-activatable MCs expressing SEAP (n=4; MC I.T.) or 5% glucose (n=3; Mock). A group of control mice also received intramuscular (I.M.) injections of MCs (n=3; MC I.M.). Plasma SEAP measurements before and for up to 2 weeks following MC administration revealed that only MC I.T. mice had elevated SEAP levels from days 3 to 14 (*p<0.05; p<0.01; *p<0.001). Data is expressed as mean±SD.
Figure 9:
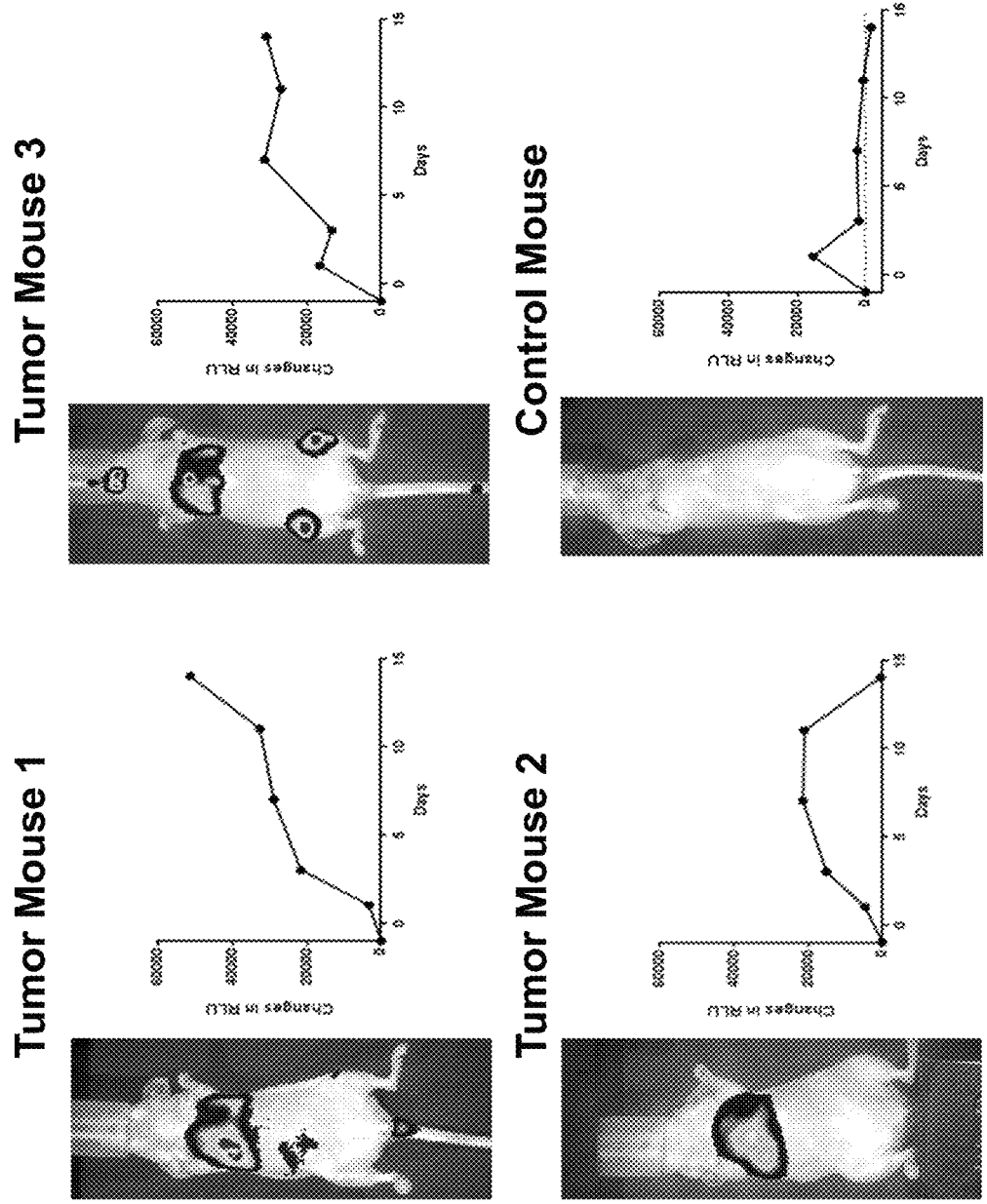
FIG. 9 illustrates representative mouse blood SEAP activity after systemic administration of tumor-specific SEAP minicircles.
Figure 10:
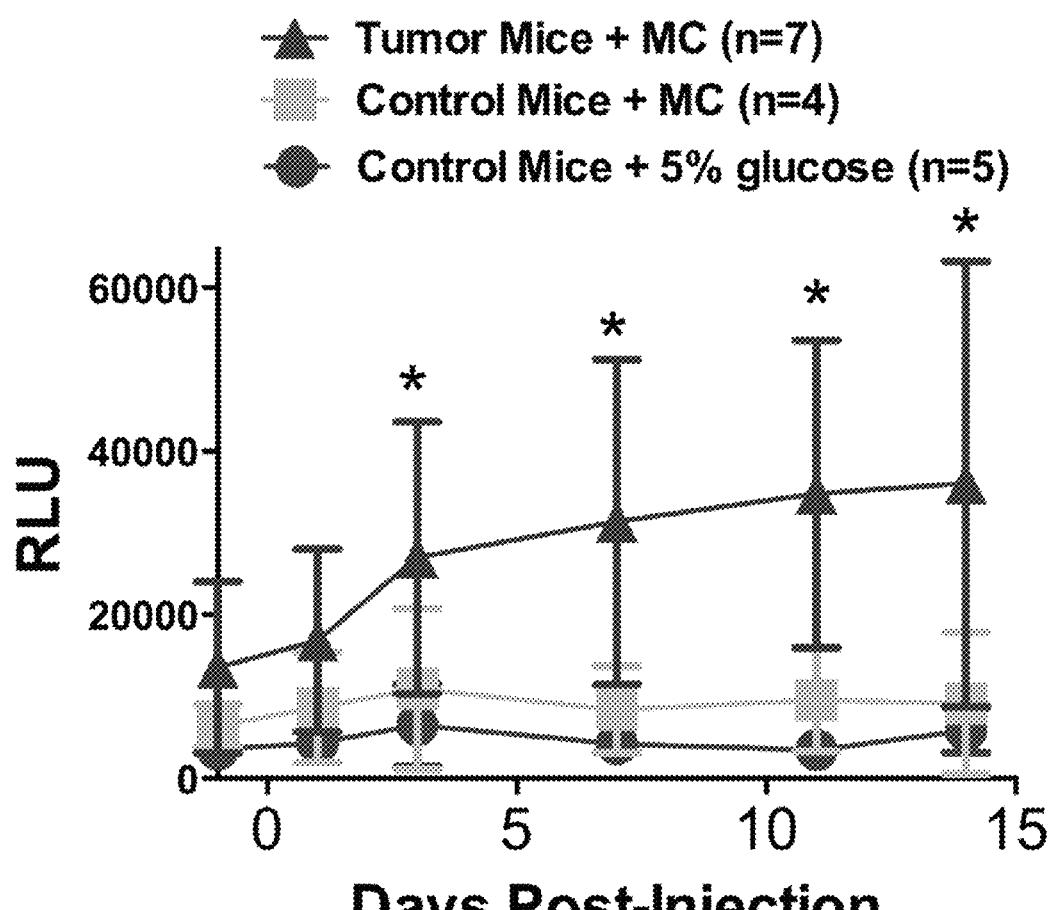
FIG. 10 is a graph illustrating blood-based cancer detection after systemic administration of tumor-specific SEAP minicircles. Significantly higher SEAP activity was detected in blood samples from tumor-bearing mice than control mice from days 3 to 14 post-injection of pSurvivin-SEAP MCs (p<0.05). No significant differences were noted between control mice receiving MC or 5% glucose. Error bars represent SD.
Figures 11, 12:
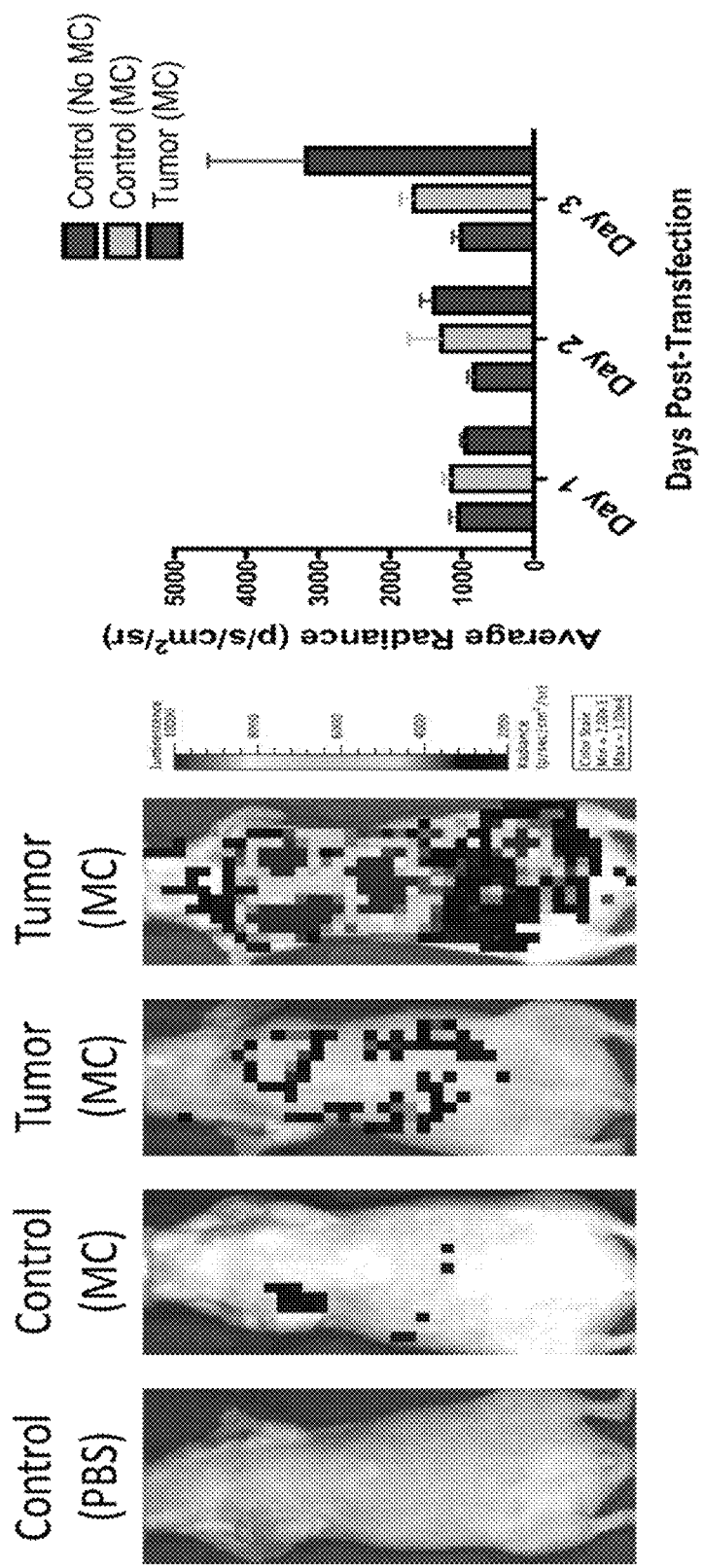
FIG. 11 is a series of digital images illustrating molecular-genetic imaging cancer detection 3 days after systemic administration of tumor-specific FLUC minicircles.
FIG. 12 is a graph illustrating molecular-genetic imaging cancer detection after systemic administration of tumor-specific FLUC minicircles.
Figures 22A, 22B:
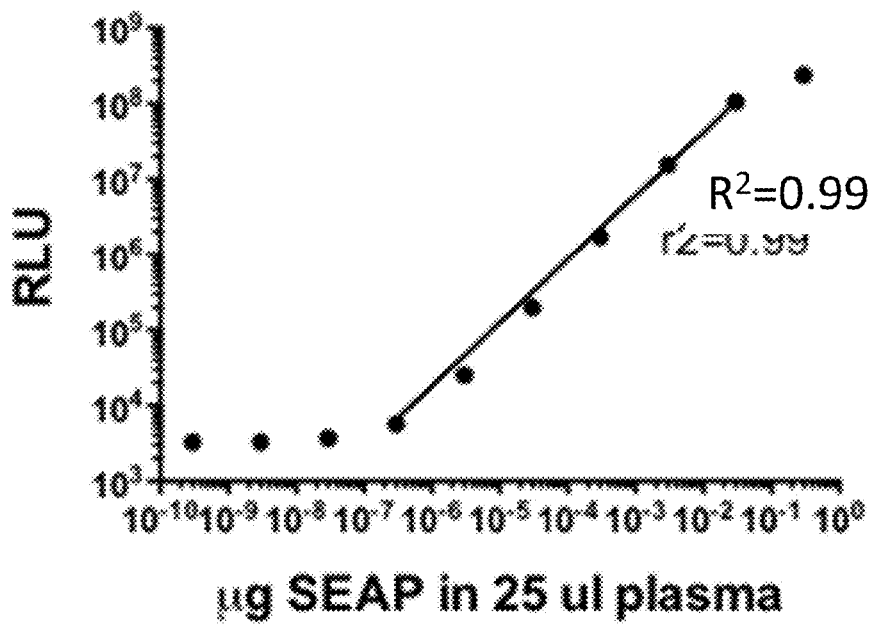
FIG. 22A illustrates a standard curve analysis of plasma SEAP assay. Triplicate samples were measured at 10-fold dilutions of SEAP in 25 μl of plasma. SEAP activity was linear over 5 orders of magnitude and showed a detection limit of approximately $3 \times 10^{-7}$ μg (0.3 μg) in 25 μl of plasma.
FIG. 22B illustrates SEAP measures over the entire linear range that were reproducible with coefficient of variance (% CV) measures less than 4%.

Intratumoral Injection of Tumor-Activatable MCs Leads to Detectable Plasma SEAP Concentration Since pSurv transcriptional activity is relatively low compared to strong promoters such as pCMV (FIGS. 18A-18D), it was determined whether direct intratumoral (I.T.) administration of tumor-activatable MCs would lead to a detectable SEAP signal in the blood. Mice bearing subcutaneous MeWo xenografts (approximately 50-80 mm$^3$) were I.T. administered 20 μg of MCs complexed with PEI (n=4) or PBS only (n=3) and SEAP concentration was measured before and at 1, 3, 5, 7, 11 and 14 days after injection (FIG. 7). Standard curve analysis showed that SEAP measurements in plasma were reproducible over 5 orders of magnitude and a SEAP concentration as low as 0.3 μg in 25 μl of plasma was detectable (FIGS. 22A and 22B). By day 3, significantly (p<0.01) increased plasma SEAP concentration was detected in mice receiving MC compared to control mice (FIGS. 15A-15D; p<0.01). Furthermore, significant differences between these two groups were noted for up to 2 weeks post-administration. The tumor specificity of expression was also examined by performing intramuscular (I.M.) MC injections on a group of mice (n=3). No significant differences were noted between tumor-bearing mice receiving I.T. 5% glucose (Mock) injections or I.M. MC-injected mice. Hence, when adequate transfection efficiency is achieved, pSurv-driven tumor-activatable MCs produce SEAP within tumors at levels sufficient enough to be detectable in the blood at multiple time points following administration.

Example 9

Figure 23:
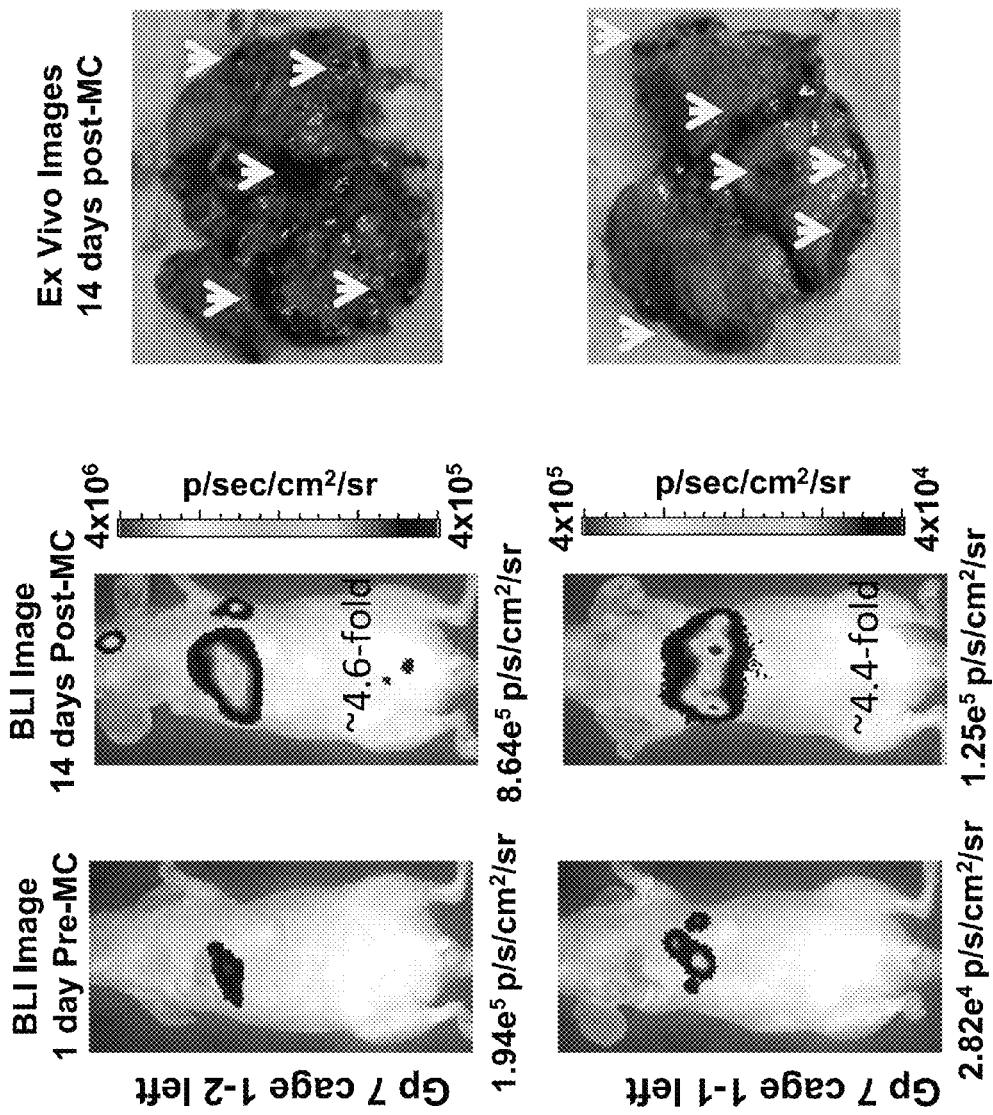
FIG. 23 illustrates tumor burden before and after MC Administration. Bioluminescence (BLI) images (left) of two representative mice (top and bottom) prior to and two weeks following MC administration and corresponding ex vivo images (right) of lungs at time of sacrifice (2 weeks after MC administration). Values below each BLI image represent average radiance in regions of interest drawn over the lungs. There is a difference in image scales for the two mice. Indicating continual tumor growth, both mice showed an approximate 4.5-fold increase in BLI signal over the 2 week period following MC administration. At sacrifice, tumors within the lungs were melanotic and multiple tumor foci throughout the lungs were observed in both mice (white arrows). Based on BLI signal changes, total tumor burden at the time of MC administration (two weeks prior to sacrifice) would have been approximately 4.5-fold less than that seen in the ex vivo images presented here.

Systemic Injection of Tumor-Activatable MCs can Identify Tumor-Bearing Subjects and Assess Tumor Burden The ability of a measurement of plasma SEAP concentration following systemic administration of tumor-activatable MCs to distinguish tumor-bearing from healthy subjects was tested. MeWo melanoma cells stably expressing a bioluminescence resonance energy transfer (BRET) fusion reporter were administered via the tail vein into irradiated nude mice (n=7) and tumor development was monitored over time with bioluminescence imaging (BLI) (FIGS. 15A-15C) and assessed qualitatively at sacrifice (FIG. 23). Although a wide range of tumor burden was observed qualitatively 3 days prior to MC administration, all tumors were primarily localized within the lungs (FIGS. 15A-15C). Following sacrifice, as expected, multiple melanotic tumor foci were noted throughout the lungs (FIG. 23). Based on changes in BLI signal, tumors would have been approximately 4.5-fold smaller at the time of MC administration (2 weeks prior).

Figure 16A:
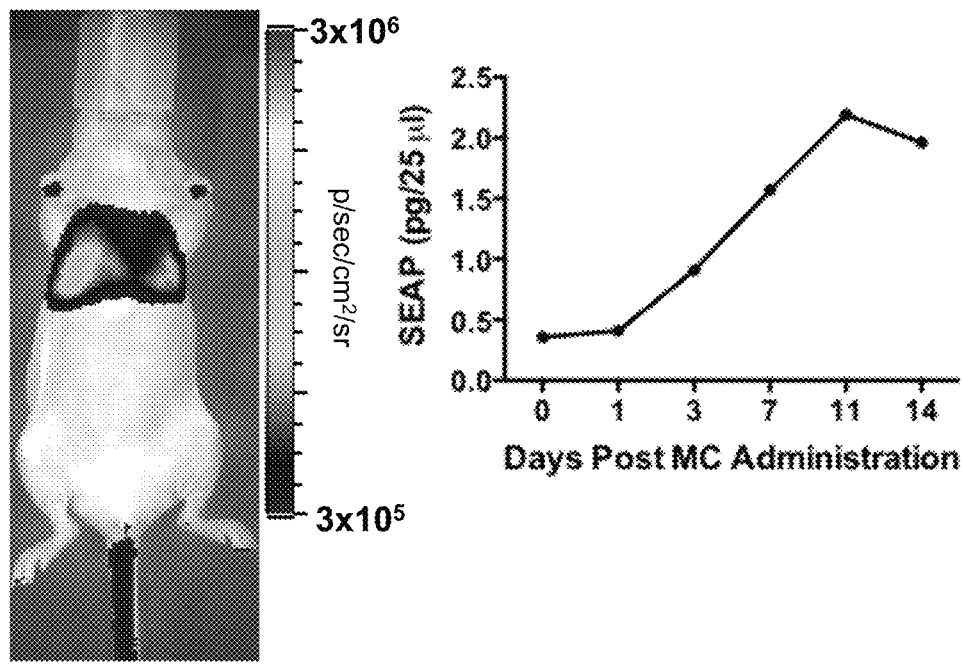
FIGS. 16A-16D illustrate the systemic delivery of tumor-activatable MCs allowing identification of tumor-bearing subjects.
Figure 16B:
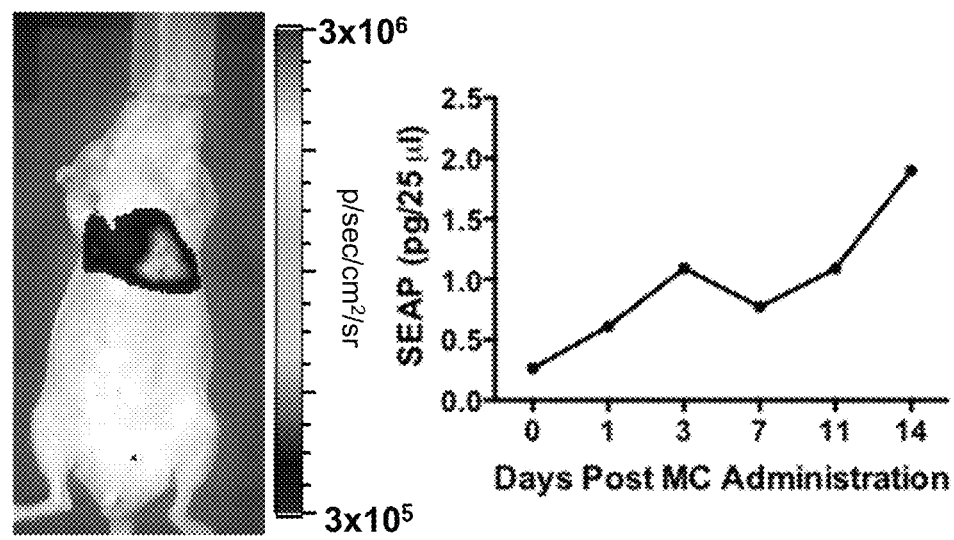
Figure 16C:
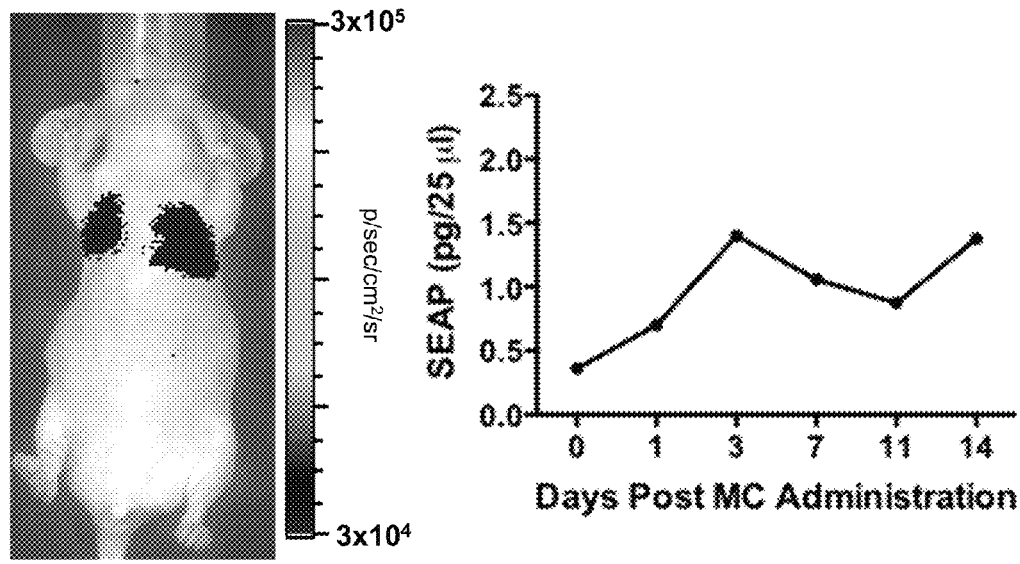
Figure 16D:
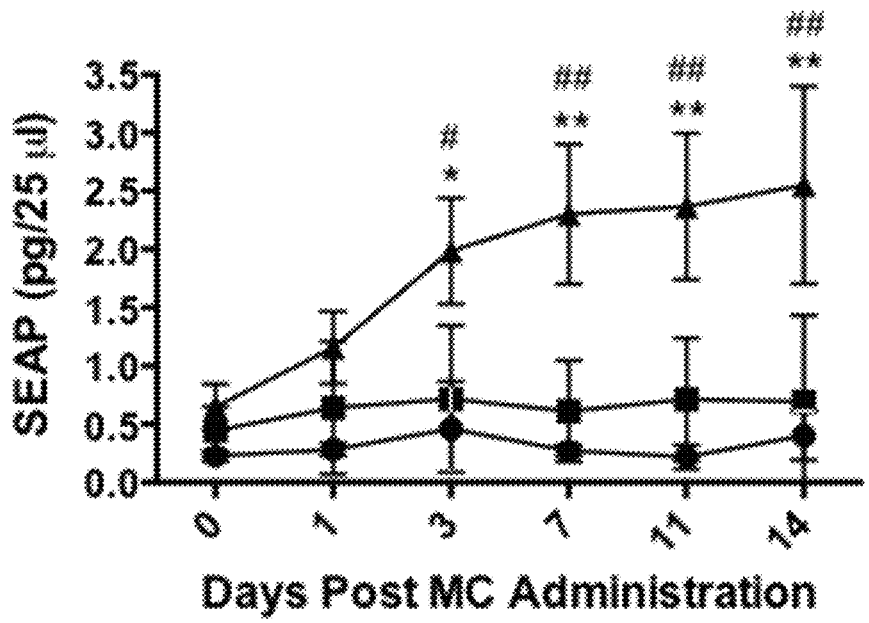

For each mouse, plasma SEAP concentration was measured before (0 days) and at 1, 3, 7, 11 and 14 days after tail-vein administration of 40 μg of MC (Tumor+MC). As control groups, healthy (tumor-free) mice also received either MC (Control+MC; n=6) or 5% glucose (Control—MC; n=5). As seen in FIGS. 16A-16C, for individual tumor-bearing mice plasma SEAP concentration was elevated post-MC injection. Regardless of tumor burden, the tumor-bearing mice showed significantly (p<0.05) higher plasma SEAP concentration profiles between days 3-14 post-administration compared to both control groups (FIG. 15). Some healthy mice receiving MC showed a slightly positive SEAP signal (most likely reflecting promoter leakiness, as also noted with pSurv in FIG. 18A-18D), overall no significant differences were noted between the two control mice groups (FIG. 16D). Therefore, measurement of plasma SEAP levels following systemic administration of tumor-activatable MCs could differentiate between tumor-bearing and healthy subjects and a wide window of opportunity (>1 week) was available to identify tumor-bearing subjects.

Since SEAP levels were elevated at multiple time points following MC administration, the cumulative shedding of SEAP into plasma was evaluated by calculating the plasma SEAP concentration area under the curve (AUC) for each mouse. Comparison of this single metric across all mice revealed no differences between the two control groups (Control+/−MC), but significantly (p<0.05) elevated values between tumor-bearing mice and both control groups (FIG. 17A).

Figure 17A:
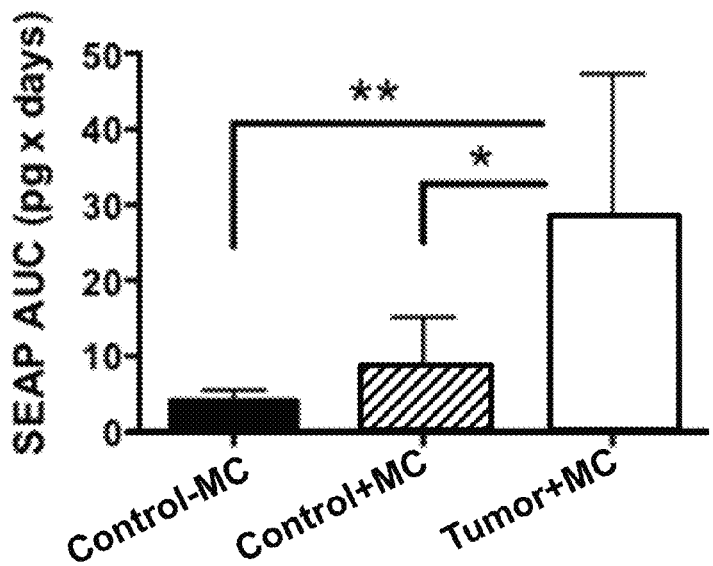
FIGS. 17A-17C illustrate that tumor-activatable MCs can robustly identify tumor-bearing subjects and measure tumor burden.
Figure 17B:
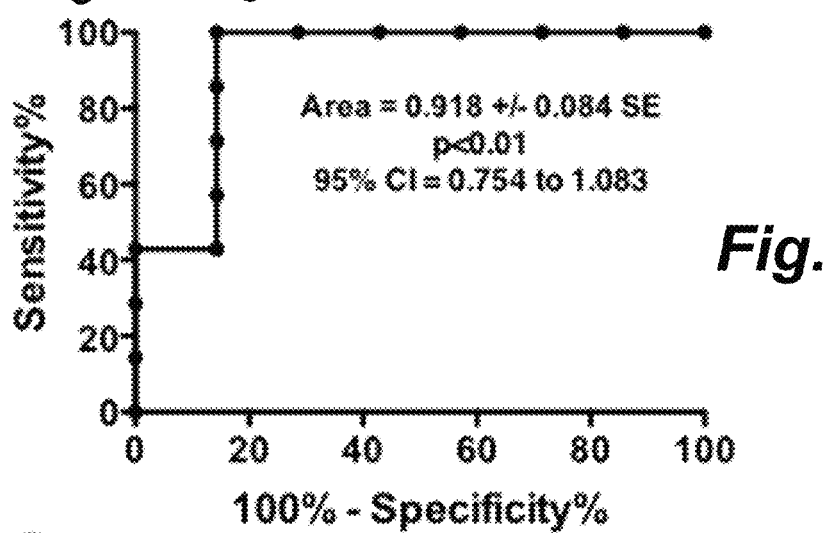

The ability of the assay to distinguish between tumor-bearing and healthy subjects by performing receiver operator-characteristic curve (ROC) analysis was evaluated, as shown in FIG. 17B. This revealed a significant (p<0.05) area of 0.918 (±0.084 SE) and a 95% confidence interval of 0.754 to 1.083. Hence, with this first generation vector used at the MC doses described, the assay was reliable in identifying tumor-bearing subjects.

Figure 17C:
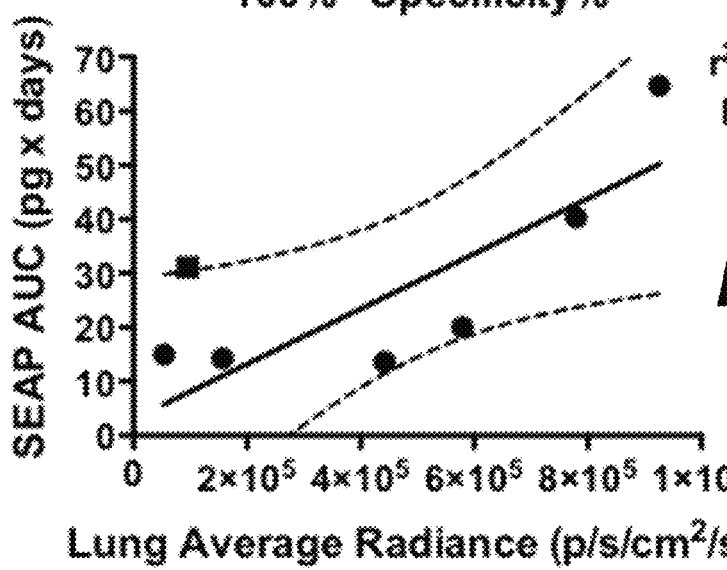
Figure 18A:
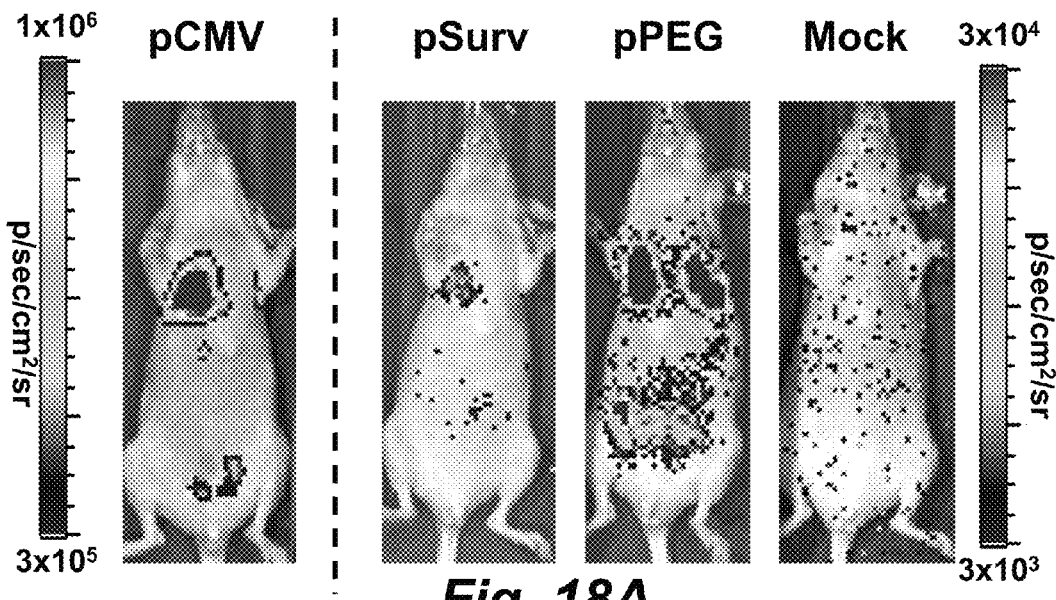
FIGS. 18A-18D illustrate comparison of promoter activities in vivo in healthy (tumor-free) mice. Mice were systemically administered plasmids (30 µg; PGL4.2 backbone; complexed with PEI (N/P=6)) expressing the bioluminescence imaging (BLI) reporter gene codon-optimized firefly luciferase (Luc2) driven by pCMV (n=3), pSurv (n=5), or pPEG (n=3). Mock-injected mice received 5% glucose (n=3). Each mouse was also co-injected with a plasmid expressing the BLI reporter gene humanized *Renilla* luciferase (hRluc) driven by pCMV to assess transfection efficiency (3 µg; 10-fold less than Luc2 plasmid mass).
Figure 18B:
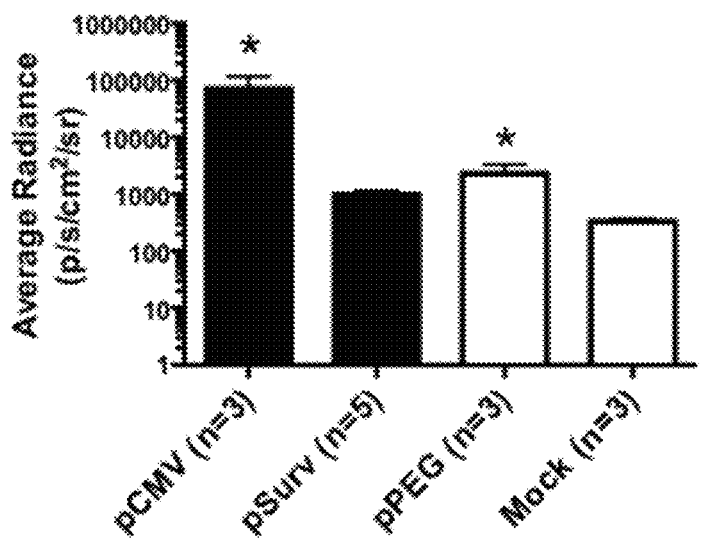
Figure 18C:
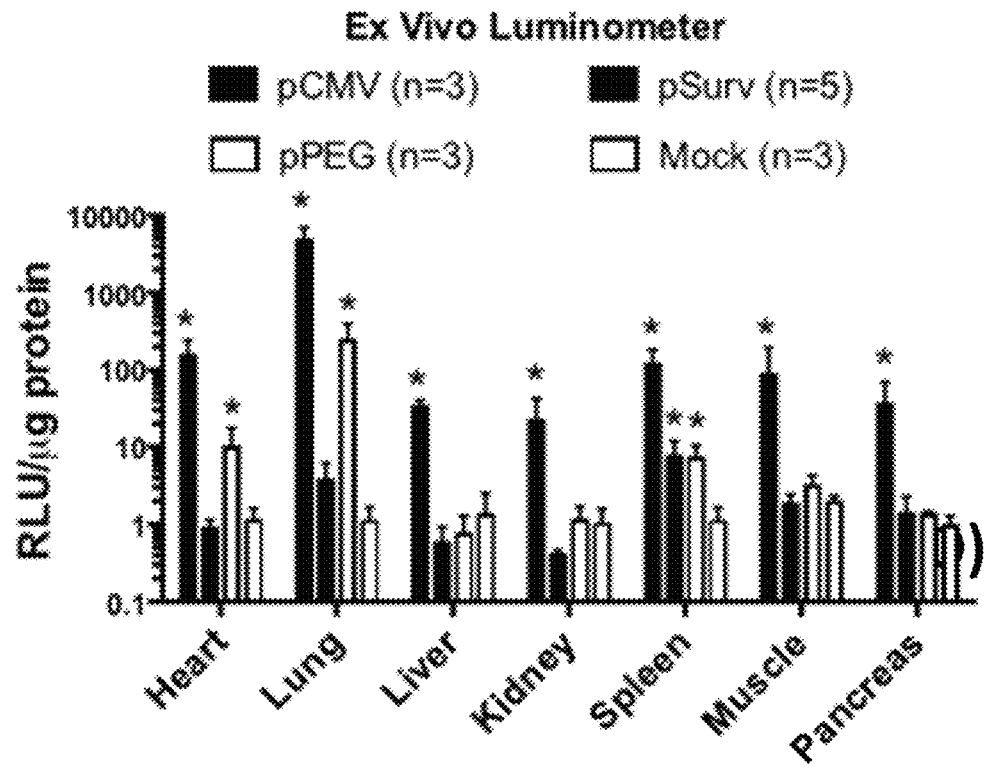
Figure 18D:
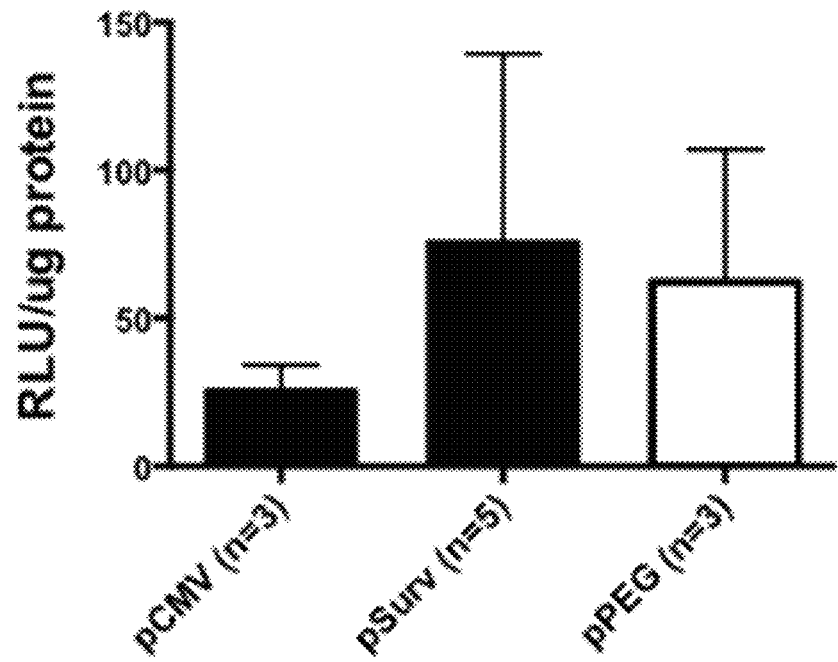

Some tumor-bearing subjects had AUC values that were only slightly above the mean of the control mice receiving MC FIG. 17A. Moreover, as shown in FIG. 16A-16C, the change of plasma SEAP concentration appeared to qualitatively correspond to the degree of tumor burden. Based on these two observations, it was hypothesized that SEAP AUCs would correlate with lung tumor burden (as assessed by BLI within 3 days prior to MC administration). Since tumors were primarily located within the lungs, and the optical BLI signal is tissue-depth dependent, the evaluation was restricted to mice with only lung tumors (n=6). One mouse with multiple metastatic foci outside the lung was excluded, although inclusion of this mouse showed an $r^2$ of 0.056 and a p-value of close to significance (p=0.0541). As expected, ROI analysis of the lung BLI signal prior to MC administration revealed a wide range of lung tumor sizes (FIG. 17). Importantly, lung tumor burden was significantly correlated with SEAP AUC values ($r^{2=0.714}$; p<0.05) (FIG. 16C). Therefore, our tumor-activatable MC system not only shows a robust ability to identify tumor-bearing subjects but provided tumor burden is restricted to one organ can also be used to evaluate disease extent.

Example 10

Statistical Analysis

All statistical analysis was performed using Prism 6.0 software (Graphpad software). Comparison of SEAP measurements from cell culture medium was performed using two-way analysis of variance (ANOVA) followed by Sidak's multiple comparisons test. Longitudinal plasma SEAP measurements from mice were compared using two-way repeated measures ANOVA followed by Tukey's multiple comparisons test. Comparison of SEAP AUC measurements across mice cohorts was performed using a one-way ANOVA followed by Tukey's multiple comparisons test. ROC analysis was performed between SEAP AUC data from tumor-bearing and healthy mice receiving MC. Finally, Pearson correlation analysis of SEAP AUC and lung tumor burden measurements was performed. For all tests a nominal p-value less than 0.05 was considered to be significant.

What is claimed:

1. A recombinant nucleic acid comprising the nucleic acid sequence of SEQ ID NO: 1.

2. A pharmaceutically acceptable composition comprising a recombinant nucleic acid minicircle vector comprising the nucleic acid sequence of SEQ ID NO: 1 and a pharmaceutically acceptable carrier.

3. A method of detecting a tumor cell in a human or non-human subject, comprising the steps of:
 (i) delivering to a subject human or non-human animal a pharmaceutically acceptable composition comprising a recombinant nucleic acid minicircle vector comprising the nucleic acid sequence of SEQ ID NO: 1; and
 (ii) detecting an expression product in the subject, wherein said expression product is secreted embryonic alkaline phosphatase (SEAP) generated from the minicircle vector comprising the nucleic acid sequence of SEQ ID NO: 1, and wherein the detection of said expression product indicates the presence of a tumor cell in the subject.

4. The method of claim 3, wherein step (ii) comprises obtaining a serum sample from the subject and determining the serum level of the expression product generated from the minicircle vector.

* * * * *

UNITED STATES PATENT AND TRADEMARK OFFICE
CERTIFICATE OF CORRECTION

PATENT NO. : 9,534,248 B2  
APPLICATION NO. : 14/480861  
DATED : January 3, 2017  
INVENTOR(S) : Sanjiv S. Gambhir and John A. Ronald Page 1 of 1

It is certified that error appears in the above-identified patent and that said Letters Patent is hereby corrected as shown below:

In the Specification

Column 1, Lines 13-20: delete the paragraph starting with "This invention" ending with "in this invention." and replace it with the following paragraph:
--This invention was made with Government support under contracts CA082214, CA135486 and CA114747 awarded by the National Institutes of Health. The Government has certain rights in the invention.--

Signed and Sealed this  
Fourth Day of February, 2020

Andrei Iancu  
*Director of the United States Patent and Trademark Office*

SEQUENCE LISTING

```
<160> NUMBER OF SEQ ID NOS: 2

<210> SEQ ID NO 1
<211> LENGTH: 4098
<212> TYPE: DNA
<213> ORGANISM: Artificial sequence
<220> FEATURE:
<223> OTHER INFORMATION: MC-pSurv-SEAP-WPRE-pA Minicircle

<400> SEQUENCE: 1
ccccaactgg ggtaaccttt gggctccccg ggcgcgacta gtaataaaat atctttattt    60
tcattacatc tgtgtgttgg tttttttgtgt gaatcgatag tactaacata cgctctccat   120
caaaacaaaa cgaaacaaaa caaactagca aaataggctg tccccagtgc aagtgcaggt   180
gccagaacat ttctctacta gtgccataga accagagaag tgagtggatg tgatgcccag   240
ctccagaagt gactccagaa caccctgttc caaagcagag gacacactga tttttttttt   300
aataggctgc aggacttact gttggtggga cgccctgctt tgcgaaggga aaggaggagt   360
ttgccctgag cacaggcccc caccctccac tgggctttcc ccagctccct tgtcttctta   420
tcacggtagt ggcccagtcc ctggcccctg actccagaag gtggccctcc tggaaaccca   480
ggtcgtgcag tcaacgatgt actcgccggg acagcgatgt ctgctgcact ccatccctcc   540
cctgttcatt tgtccttcat gcccgtctgg agtagatgct ttttgcagag gtggcaccct   600
gtaaagctct cctgtctgac tttttttttt ttttttagact gagttttgct cttgttgcct   660
aggctggagt gcaatggcac aatctcagct cactgcaccc tctgcctccc gggttcaagc   720
gattctcctg cctcagcctc ccgagtagtt gggattacag gcatgcacca ccacgcccag   780 ctaattttg tattttagt agagacaagg tttcaccgtg atggccaggc tggtcttgaa    840
ctccaggact caagtgatgc tcctgcctag gcctctcaaa gtgttgggat tacaggcgtg   900
agccactgca cccggcctgc acgcgttctt tgaaagcagt cgaggggcg ctaggtgtgg   960
```

```
gcagggacga gctggcgcgg cgtcgctggg tgcaccgcga ccacgggcag agccacgcgg    1020
cgggaggact acaactcccg gcacaccccg cgccgccccg cctctactcc cagaaggccg    1080 cgggggggtgg accgcctaag agggcgtgcg ctcccgacat gccccgcggc gcgccattaa    1140
ccgccagatt tgaatcgcgg gacccgttgg cagaggtggg aattcaccgg tcaccatggt    1200
tctggggccc tgcatgctgc tgctgctgct gctgctgggc ctgaggctac agctctccct    1260
gggcatcatc ccagttgagg aggagaaccc ggacttctgg aaccgcgagg cagccgaggc    1320
cctgggtgcc gccaagaagc tgcagcctgc acagacagcc gccaagaacc tcatcatctt    1380
cctgggcgat gggatggggg tgtctacggt gacagctgcc aggatcctaa aagggcagaa    1440
gaaggacaaa ctggggcctg agataccccct ggctatggac cgcttcccat atgtggctct    1500
gtccaagaca tacaatgtag acaaacatgt gccagacagt ggagccacag ccacggccta    1560
cctgtgcggg gtcaagggca acttccagac cattggcttg agtgcagccg cccgctttaa    1620
ccagtgcaac acgacacgcg gcaacgaggt catctccgtg atgaatcggg ccaagaaagc    1680
agggaagtca gtgggagtgg taaccaccac acgagtgcag cacgcctcgc cagccggcac    1740
ctacgcccac acggtgaacc gcaactggta ctcggacgcc gacgtgcctg cctcggcccg    1800
ccaggagggg tgccaggaca tcgctacgca gctcatctcc aacatggaca ttgatgtgat    1860
cctgggtgga ggccgaaagt acatgtttcg catgggaacc ccagaccctg agtacccaga    1920
tgactacagc caaggtggga ccaggctgga cgggaagaat ctggtgcagg aatggctggc    1980
gaagcgccag ggtgcccggt atgtgtggaa ccgcactgag ctcatgcagg cttccctgga    2040
cccgtctgtg acccatctca tgggtctctt tgagcctgga gacatgaaat acgagatcca    2100
ccgagactcc acactggacc cctccctgat ggagatgaca gaggctgccc tgcgcctgct    2160
gagcaggaac ccccgcggct tcttcctctt cgtggagggt ggtcgcatcg accacggtca    2220
tcacgaaagc agggcttacc gggcactgac tgagacgatc atgttcgacg acgccattga    2280
gagggcgggc cagctcacca gcgaggagga cacgctgagc ctcgtcactg ccgaccactc    2340
ccacgtcttc tccttcggag gctacccccct gcgagggagc tccatcttcg ggctggcccc    2400
tggcaaggcc cgggacagga aggcctacac ggtcctccta tacggaaacg gtccaggcta    2460
tgtgctcaag gacggcgccc ggccggatgt taccgagagc gagagcggga gccccgagta    2520
tcggcagcag tcagcagtgc ccctggacga agagacccac gcaggcgagg acgtggcggt    2580
gttcgcgcgc ggcccgcagg cgcacctggt tcacggcgtg caggagcaga ccttcatagc    2640
gcacgtcatg gccttcgccg cctgcctgga gccctacacc gctgcgacc tggcgccccc    2700 cgccggcacc accgacgccg cgcacccggg gcggtcccgg tccaagcgtc tggattgagc    2760
tagcttcgaa tttaaatcgg atccctgcag gagctcgtcg acaatcaacc tctggattac    2820
aaaatttgtg aaagattgac tggtattctt aactatgttg ctccttttac gctatgtgga    2880
tacgctgctt taatgccttt gtatcatgct attgcttccc gtatggcttt cattttctcc    2940
tccttgtata atcctggtt gctgtctctt tatgaggagt tgtggcccgt tgtcaggcaa    3000
cgtggcgtgg tgtgcactgt gtttgctgac gcaaccccca ctggttgggg cattgccacc    3060
acctgtcagc tcctttccgg gactttcgct ttccccctcc ctattgccac ggcggaactc    3120
atcgccgcct gccttgcccg ctgctggaca ggggctcggc tgttgggcac tgacaattcc    3180
gtggtgttgt cggggaaatc atcgtccttt ccttggctgc tcgcctgtgt tgccacctgg    3240
attctgcgcg ggacgtcctt ctgctacgtc ccttcggccc tcaatccagc ggaccttcct    3300
```

```
tcccgcggcc tgctgccggc tctgcggcct cttccgcgtc ttcgccttcg ccctcagacg    3360
agtcggatct ccctttgggc cgcctccccg cctggtacct ttaagaccaa tgacttacaa    3420
ggcagctgta gatcttagcc acttttttaaa agaaaagggg ggactggaag ggctaattca    3480
ctcccaacga aaataagatc tgcttttttgc ttgtactggg tctctctggt tagaccagat    3540
ctgagcctgg gagctctctg gctaactagg gaacccactg cttaagcctc aataaagctt    3600
gccttgagtg cttcaagtag tgtgtgcccg tctgttgtgt gactctggta actagagatc    3660
cctcagaccc ttttagtcag tgtggaaaat ctctagcagt agtagttcat gtcatcttat    3720
tattcagtat ttataacttg caaagaaatg aatatcagag agtgagagga acttgtttat    3780
tgcagcttat aatggttaca aataaagcaa tagcatcaca aatttcacaa ataaagcatt    3840 ttttttcactg cattctagtt gtggtttgtc caaactcatc aatgtatctt atcatgtctg    3900
gctctagcta tcccgcccct aactccgccc agttccgccc attctccgcc cctcccgccc    3960
ctaactccgc ccaatggctg actaattttt tttatttatg cagaggccga ggccgcctcg    4020
gcctctgagc tattccagaa gtagtgagga ggcttttttg gaggcctaga cttttgcaga    4080
tcgacccatg ggggcccg                                                 4098

<210> SEQ ID NO 2
<211> LENGTH: 4256
<212> TYPE: DNA
<213> ORGANISM: Artificial sequence
<220> FEATURE:
<223> OTHER INFORMATION: MC-pSurv-Luc2-WPRE-pA

<400> SEQUENCE: 2
ccccaactgg ggtaaccttt gggctccccg ggcgcgacta gtaataaaat atctttattt      60
tcattacatc tgtgtgttgg ttttttgtgt gaatcgatag tactaacata cgctctccat     120
caaaacaaaa cgaaacaaaa caaactagca aaataggctg tccccagtgc aagtgcaggt     180
gccagaacat ttctctacta gtgaattgat gccatagaac cagagaagtg agtggatgtg     240
atgcccagct ccagaagtga ctccagaaca ccctgttcca aagcagagga cacactgatt     300 tttttttaa taggctgcag gacttactgt tggtgggacg ccctgctttg cgaagggaaa     360
ggaggagttt gccctgagca caggccccca ccctccactg ggctttcccc agctcccttg     420
tcttcttatc acgtagtggg cccagtccct ggccctgac tccagaaggt ggccctcctg      480
gaaacccagg tcgtgcagtc aacgatgtac tcgccgggac agcgatgtct gctgcactcc     540
atccctcccc tgttcatttg tccttcatgc ccgtctggag tagatgcttt ttgcagaggt     600
ggcaccctgt aaagctctcc tgtctgactt tttttttttt tttagactga gttttgctct     660
tgttgcctag gctggagtgc aatggcacaa tctcagctca ctgcaccctc tgcctcccgg     720
gttcaagcga ttctcctgcc tcagcctccc gagtagttgg gattacaggc atgcaccacc     780
acgcccagct aatttttgta tttttagtag agacaaggtt tcaccgtgat ggccaggctg     840
gtcttgaact ccaggactca agtgatgctc ctgcctaggc ctctcaaagt gttgggatta     900
caggcgtgag ccactgcacc cggcctgcac gcgttctttg aaagcagtcg agggggcgct     960
aggtgtgggc aggacgagc tggcgcggcg tcgctgggtg caccgcgacc acgggcagag    1020
ccacgcggcg ggaggactac aactcccggc acacccgcg ccgccccgcc tctactccca    1080
gaaggccgcg gggggtggac cgcctaagag ggcgtgcgct cccgacatgc ccgcggcgc    1140 gccattaacc gccagatttg aatcgcggga cccgttggca gaggtggaag cttgcaatc    1200 cggtactgtt ggtaaagcca ccatggaaga tgccaaaaac attaagaagg gcccagcgcc    1260
```

```
attctaccca ctcgaagacg ggaccgccgg cgagcagctg cacaaagcca tgaagcgcta    1320
cgccctggtg cccggcacca tcgcctttac cgacgcacat atcgaggtgg acattaccta    1380
cgccgagtac ttcgagatga gcgttcggct ggcagaagct atgaagcgct atgggctgaa    1440
tacaaaccat cggatcgtgg tgtgcagcga gaatagcttg cagttcttca tgcccgtgtt    1500
gggtgccctg ttcatcggtg tggctgtggc cccagctaac gacatctaca acgagcgcga    1560
gctgctgaac agcatgggca tcagccagcc caccgtcgta ttcgtgagca agaaagggct    1620
gcaaaagatc ctcaacgtgc aaaagaagct accgatcata caaaagatca tcatcatgga    1680
tagcaagacc gactaccagg gcttccaaag catgtacacc ttcgtgactt cccatttgcc    1740
acccggcttc aacgagtacg acttcgtgcc cgagagcttc gaccgggaca aaaccatcgc    1800
cctgatcatg aacagtagtg gcagtaccgg attgcccaag ggcgtagccc taccgcaccg    1860
caccgcttgt gtccgattca gtcatgcccg cgaccccatc ttcggcaacc agatcatccc    1920
cgacaccgct atcctcagcg tggtgccatt tcaccacggc ttcggcatgt tcaccacgct    1980
gggctacttg atctgcggct tcgggtcgt gctcatgtac cgcttcgagg aggagctatt    2040
cttgcgcagc ttgcaagact ataagattca atctgccctg ctggtgccca cactatttag    2100
cttcttcgct aagagcactc tcatcgacaa gtacgaccta agcaacttgc acgagatcgc    2160
cagcggcggg gcgccgctca gcaaggaggt aggtgaggcc gtggccaaac gcttccacct    2220
accaggcatc cgccagggct acggcctgac agaaacaacc agcgccattc tgatcacccc    2280
cgaaggggac gacaagcctg cgcagtagg caaggtggtg cccttcttcg aggctaaggt    2340
ggtggacttg gacaccggta agacactggg tgtgaaccag cgcggcgagc tgtgcgtccg    2400
tggccccatg atcatgagcg gctacgttaa caaccccgag gctacaaacg ctctcatcga    2460
caaggacggc tggctgcaca gcggcgacat cgcctactgg gacgaggacg agcacttctt    2520
catcgtggac cggctgaaga gcctgatcaa atacaagggc taccaggtag ccccagccga    2580
actggagagc atcctgctgc aacaccccaa catcttcgac gccggggtcg ccggcctgcc    2640
cgacgacgat gccggcgagc tgcccgccgc agtcgtcgtg ctggaacacg gtaaaaccat    2700
gaccgagaag gagatcgtgg actatgtggc cagccaggtt acaaccgcca agaagctgcg    2760
cggtggtgtt gtgttcgtgg acgaggtgcc taaaggactg accggcaagt tggacgcccg    2820
caagatccgc gagattctca ttaaggccaa gaagggcggc aagatcgccg tgtaatctag    2880
agctagcgaa ttcagatctg atatctctag agtcgagcta gcttcgaatt taaatcggat    2940
ccctgcagga gctcgtcgac aatcaacctc tggattacaa aatttgtgaa agattgactg    3000
gtattcttaa ctatgttgct cctttacgc tatgtggata cgctgcttta atgcctttgt    3060
atcatgctat tgcttcccgt atggctttca ttttctcctc cttgtataaa tcctggttgc    3120
tgtctcttta tgaggagttg tggcccgttg tcaggcaacg tggcgtggtg tgcactgtgt    3180
ttgctgacgc aacccccact ggttgggca ttgccaccac ctgtcagctc ctttccggga    3240
ctttcgcttt ccccctccct attgccacgg cggaactcat cgccgcctgc cttgcccgct    3300
gctggacagg ggctcggctg ttgggcactg acaattccgt ggtgttgtcg gggaaatcat    3360
cgtccttttc ttggctgctc gcctgtgttg ccacctggat tctgcgcggg acgtccttct    3420
gctacgtccc ttcggccctc aatccagcgg accttccttc ccgcggcctg ctgccggctc    3480
tgcggcctct tccgcgtctt cgccttcgcc ctcagacgag tcggatctcc ctttgggccg    3540
cctccccgcc tggtaccttt aagaccaatg acttacaagg cagctgtaga tcttagccac    3600
```

```
ttttaaaag   aaaagggggg   actggaaggg   ctaattcact   cccaacgaaa   ataagatctg    3660 cttttgctt   gtactgggtc   tctctggtta   gaccagatct   gagcctggga   gctctctggc    3720
taactaggga  acccactgct   taagcctcaa   taaagcttgc   cttgagtgct   tcaagtagtg    3780
tgtgcccgtc  tgttgtgtga   ctctggtaac   tagagatccc   tcagacccttt  ttagtcagtg   3840 tggaaaatct  ctagcagtag   tagttcatgt   catcttatta   ttcagtattt   ataacttgca    3900
aagaaatgaa  tatcagagag   tgagaggaac   ttgtttattg   cagcttataa   tggttacaaa    3960
taaagcaata  gcatcacaaa   tttcacaaat   aaagcatttt   tttcactgca   ttctagttgt    4020
ggtttgtcca  aactcatcaa   tgtatcttat   catgtctggc   tctagctatc   ccgcccctaa    4080
ctccgcccag  ttccgcccat   tctccgcccc   tcccgcccct   aactccgccc   aatggctgac    4140 taatttttt   tatttatgca   gaggccgagg   ccgcctcggc   ctctgagcta   ttccagaagt    4200
agtgaggagg  ctttttgga    ggcctagact   tttgcagatc   gacccatggg   ggcccg        4256
```